US012685460B2

(12) United States Patent
    Pereira et al.

(10) Patent No.: US 12,685,460 B2
(45) Date of Patent: Jul. 21, 2026

(54) SYSTEM FOR DETERMINING PATIENT SUPPORT APPARATUS AND MEDICAL DEVICE LOCATION

(71) Applicant: Stryker Corporation, Kalamazoo, MI (US)

(72) Inventors: Celso Henrique Farnese Pires Pereira, Portage, MI (US); Jerald A. Trepanier, Augusta, MI (US); Krishna Sandeep Bhimavarapu, Kalamazoo, MI (US); Kirby M. Neihouser, Portage, MI (US); Thomas Deeds, Seattle, WA (US); Madhu Sandeep Thota, Portage, MI (US); Madhu Thomas, London (CA)

(73) Assignee: Stryker Corporation, Portage, MI (US)

( * ) Notice: Subject to any disclaimer, the term of this patent is extended or adjusted under 35 U.S.C. 154(b) by 574 days.

(21) Appl. No.: 18/028,590

(22) PCT Filed: Feb. 24, 2022

(86) PCT No.: PCT/US2022/017616
    § 371 (c)(1),
    (2) Date: Mar. 27, 2023

(87) PCT Pub. No.: WO2022/182816
    PCT Pub. Date: Sep. 1, 2022

(65) Prior Publication Data
    US 2023/0337941 A1      Oct. 26, 2023

Related U.S. Application Data

(60) Provisional application No. 63/306,279, filed on Feb. 3, 2022, provisional application No. 63/245,279, filed
    (Continued)

(51) Int. Cl.
    *G16H 40/63*      (2018.01)
    *A61B 5/11*       (2006.01)
    (Continued)

(52) U.S. Cl.
    CPC .......... *A61B 5/1115* (2013.01); *A61G 7/0506* (2013.01); *G16H 40/20* (2018.01); *G16H 40/67* (2018.01); *G16H 40/63* (2018.01)

(58) Field of Classification Search
    CPC .... A61B 5/1115; A61G 7/0506; G16H 40/20; G16H 40/67; G16H 40/63
    See application file for complete search history.

(56) References Cited

U.S. PATENT DOCUMENTS

| | | | |
|---|---|---|---|
| 7,242,306 B2 | 7/2007 | Wildman et al. | |
| 7,570,152 B2 | 8/2009 | Smith et al. | |
(Continued)

FOREIGN PATENT DOCUMENTS

| | | |
|---|---|---|
| WO | 1994027544 A2 | 12/1994 |
| WO | 2021228946 A1 | 11/2021 |
(Continued)

OTHER PUBLICATIONS

PCT International Search Report dated Jun. 14, 2022, for International application No. PCT/US2022/017616.

*Primary Examiner* — Wesley L Kim
*Assistant Examiner* — Fabian Botello
(74) *Attorney, Agent, or Firm* — Gardner, Linn, Burkhart & Ondersma LLP

(57)          ABSTRACT

A system includes a patient support apparatus and a plurality of location transceivers. One of more of the location transceivers are positioned onboard the patient support apparatus and one or more are positioned at fixed locations within the room. The onboard location transceivers determine their location with respect to the off-board location transceivers,
(Continued)

or vice versa, and use this location information to determine the position of the tagged medical device with respect to a volume of space. If the tagged medical device is inside the volume of space, a controller may: (a) associate the tagged medical device with the patient support apparatus, a patient, a room identifier, and/or a room bay identifier; (b) allow the tagged medical device to join a communication network, and/or (c) forward data from the tagged medical device to a remotely positioned server.

8 Claims, 12 Drawing Sheets

Related U.S. Application Data on Sep. 17, 2021, provisional application No. 63/245,289, filed on Sep. 17, 2021, provisional application No. 63/245,245, filed on Sep. 17, 2021, provisional application No. 63/193,777, filed on May 27, 2021, provisional application No. 63/161,175, filed on Mar. 15, 2021, provisional application No. 63/154,677, filed on Feb. 27, 2021.

(51) Int. Cl.

| | |
|---|---|
| *A61G 7/05* | (2006.01) |
| *G16H 40/20* | (2018.01) |
| *G16H 40/67* | (2018.01) |

(56) References Cited

U.S. PATENT DOCUMENTS

| | | | |
|---|---|---|---|
| 7,852,208 | B2 | 12/2010 | Collins, Jr. et al. |
| 8,082,160 | B2 | 12/2011 | Collins, Jr. et al. |
| 8,334,777 | B2 | 12/2012 | Wilson et al. |
| 8,334,779 | B2 | 12/2012 | Zerhusen et al. |
| 8,727,216 | B2 | 5/2014 | Graves et al. |
| 8,756,078 | B2 | 6/2014 | Collins, Jr. et al. |
| 8,786,402 | B2 | 7/2014 | Barnes |
| 9,320,662 | B2 | 4/2016 | Hayes et al. |
| 9,427,365 | B2 | 8/2016 | Richards et al. |
| 9,569,591 | B2 | 2/2017 | Vanderpohl, III |
| 9,571,985 | B2 | 2/2017 | Bottazzi et al. |
| 9,788,151 | B2 | 10/2017 | Duan et al. |
| 9,977,121 | B1 * | 5/2018 | Fink ......................... H01Q 25/00 |
| 9,999,375 | B2 * | 6/2018 | Hayes ................... A61B 5/6892 |
| 10,064,012 | B1 | 8/2018 | Boston et al. |
| 10,474,808 | B2 | 11/2019 | Huster |
| 10,486,646 | B2 | 11/2019 | Ledvina et al. |
| 10,608,699 | B2 | 3/2020 | Nabki et al. |
| 10,759,389 | B2 | 9/2020 | Edvina et al. |
| 10,811,136 | B2 | 10/2020 | Bhimavarapu et al. |
| 10,846,961 | B2 | 11/2020 | de Perthuis et al. |
| 11,019,195 | B2 | 5/2021 | Ledvina et al. |
| 11,026,067 | B2 | 6/2021 | Martin et al. |
| 11,082,809 | B1 | 8/2021 | Burowski et al. |
| 11,153,810 | B2 | 10/2021 | Yoon et al. |
| 11,289,194 | B1 | 3/2022 | Pipher et al. |
| 11,301,651 | B2 | 4/2022 | Studerus et al. |
| 11,343,645 | B2 | 5/2022 | Yoon et al. |
| 11,378,644 | B2 | 7/2022 | Hsieh |
| 11,400,889 | B2 | 8/2022 | Parthasarathi et al. |
| 11,610,671 | B2 | 3/2023 | Hochworter |
| 2002/0014951 | A1 | 2/2002 | Kramer et al. |
| 2002/0167417 | A1 | 11/2002 | Welles et al. |
| 2005/0185799 | A1 | 8/2005 | Bertram |
| 2007/0135866 | A1 | 6/2007 | Baker et al. |
| 2007/0247316 | A1 | 10/2007 | Wildman et al. |
| 2008/0312971 | A2 | 12/2008 | Rosow et al. |
| 2010/0001838 | A1 | 1/2010 | Miodownik et al. |
| 2011/0208541 | A1 | 8/2011 | Wilson et al. |
| 2014/0080413 | A1 * | 3/2014 | Hayes ................... H04B 5/266 |
| | | | 455/41.1 |
| 2014/0297327 | A1 | 10/2014 | Heil et al. |
| 2014/0320290 | A1 | 10/2014 | Reeder et al. |
| 2015/0099458 | A1 | 4/2015 | Weisner et al. |
| 2016/0038361 | A1 | 2/2016 | Bhimavarapu et al. |
| 2016/0140307 | A1 | 5/2016 | Brosnan et al. |
| 2017/0287316 | A1 | 10/2017 | Wildman et al. |
| 2018/0174682 | A1 | 6/2018 | Johnson et al. |
| 2018/0185221 | A1 | 7/2018 | Hayes et al. |
| 2020/0335187 | A1 | 10/2020 | Lefkofsky et al. |
| 2021/0014677 | A1 | 1/2021 | Han et al. |
| 2021/0065885 | A1 * | 3/2021 | Receveur .............. G16H 40/67 |
| 2021/0175638 | A1 * | 6/2021 | Povalac .................. G01S 3/043 |
| 2021/0266710 | A1 | 8/2021 | Martin et al. |
| 2021/0360366 | A1 | 11/2021 | Bailey et al. |
| 2021/0400439 | A1 | 12/2021 | Troester et al. |
| 2022/0053292 | A1 | 2/2022 | Hoff et al. |
| 2022/0082676 | A1 | 3/2022 | Lee et al. |
| 2022/0137204 | A1 | 5/2022 | Nguyen et al. |
| 2022/0139133 | A1 | 5/2022 | Schober et al. |
| 2022/0241124 | A1 | 8/2022 | Bhimavarapu et al. |
| 2023/0049776 | A1 * | 2/2023 | Freeman ............... A61B 5/339 |

FOREIGN PATENT DOCUMENTS

| | | | |
|---|---|---|---|
| WO | 2021236649 | A1 | 11/2021 |
| WO | 2022086515 | A1 | 4/2022 |

* cited by examiner

SYSTEM FOR DETERMINING PATIENT SUPPORT APPARATUS AND MEDICAL DEVICE LOCATION

CROSS-REFERENCE TO RELATED APPLICATIONS

This application claims priority to U.S. provisional patent application Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION; U.S. provisional patent application Ser. No. 63/161,175 filed Mar. 15, 2021, by inventors Krishna Bhimavarapu et al. and entitled EXERCISE DEVICE AND PATIENT SUPPORT APPARATUS; U.S. provisional patent application Ser. No. 63/193,777 filed May 27, 2021, by inventors Thomas Deeds et al. and entitled SYSTEM FOR ASSOCIATING MEDICAL DEVICE DATA; U.S. provisional patent application Ser. No. 63/245,245 filed Sep. 17, 2021, by inventors Kirby Neihouser et al. and entitled SYSTEM FOR LOCATING PATIENT SUPPORT APPARATUSES; U.S. provisional patent application Ser. No. 63/245,279 filed Sep. 17, 2021, by inventors Jerald Trepanier et al. and entitled PATIENT SUPPORT APPARATUSES WITH PATIENT MONITORING; and U.S. provisional patent application Ser. No. 63/245,289 filed Sep. 17, 2021, by inventors Madhu Thota et al. and entitled PATIENT SUPPORT APPARATUS COMMUNICATION AND LOCATION SYSTEM; U.S. provisional patent application Ser. No. 63/306,279 filed Feb. 3, 2022, by inventors Madhu Thota et al. and entitled COMMUNICATION SYSTEM FOR PATIENT SUPPORT APPARATUSES, the complete disclosures of all of which are incorporated herein by reference.

BACKGROUND

The present disclosure relates to patient support apparatuses, such as beds, cots, stretchers, recliners, or the like. More specifically, the present disclosure relates to a system for automatically determining the location of devices relative to a patient support apparatus and/or a defined volume of space within a room in which the device is positioned.

Devices are often used with a patient while the patient is positioned on a patient support apparatus. Those devices typically generate data regarding the patient that may be desirably forwarded to an electronic medical records server. In order for that data to be assigned to the medical records of the correct patient, one or more manual steps are typically required by a caregiver to associate the data from a particular device with a particular patient. In some cases, patient identity information is input into the device itself, and this identity information is transmitted with other data from the device to the EMR. This method requires that the transmitted patient data be properly secured against unauthorized disclosure so that unauthorized individuals do not gain access to the patient identify and his or her data.

SUMMARY

According to various embodiments, the present disclosure is directed to a system that overcomes past issues with associating data from medical devices with the correct patient and/or with a correct proxy for the patient (e.g. the patient support apparatus to which the patient is assigned, the room and/or room bay to which the patient is assigned, etc.). That is, the present disclosure provides a system and method for automatically associating a medical device with the patient (or a proxy for the patient) if the medical device is positioned within a predetermined volume of space. The predetermined volume of space may be defined with respect to the patient support apparatus such that is moves as the patient support apparatus moves, or it may be defined in a fixed relationship with respect to a room, or other location, of a healthcare facility such that it does not change as the patient support apparatus moves. In some embodiments, a controller prevents data from the medical device from being transmitted to a local area network when the medical device is outside of the volume of space, and allows the data to be transmitted when it is inside the volume of space. In alternative embodiments, the controller may associate the data with the patient (or the patient's proxy) if the medical device is inside the volume of space, but not associate the data with the patient (or the patient's proxy) if the medical device is outside of the volume of space. The determination of the location of the medical device with respect to the volume of space may utilize one or more location transceivers that are positioned on-board the patient support apparatus, and/or one or more location transceivers that are positioned off-board the patient support apparatus. In some embodiments, one or more of the off-board location transceivers may be built into one or more headwall units that the patient support apparatus uses to wirelessly communicate with a nurse call system outlet. The location transceivers may utilize ultra-wideband, Bluetooth, and/or other communication technologies for determining the location of the medical device.

According to one embodiment of the present disclosure, a system for automatically detecting medical devices positioned within a room of a healthcare facility is provided. The system includes a patient support apparatus, a headwall unit, a network transceiver, and a controller. The patient support apparatus includes a support surface adapted to support a person; a microphone adapted to convert sound from a patient positioned on the patient support apparatus into audio signals; a first transceiver adapted to wirelessly transmit the audio signals; and a first location transceiver adapted to generate a first location estimate of a tagged medical device with respect to the patient support apparatus. The headwall unit includes a second transceiver adapted to wirelessly receive the audio signals from the first transceiver of the patient support apparatus; a second location transceiver adapted to generate a second location estimate of the tagged medical device with respect to the headwall unit; and a nurse call interface coupled to a nurse call system, the nurse call interface adapted to forward the audio signals to the nurse call system. The controller is adapted to use the first and second location estimates to determine if the tagged medical device is inside or outside of a volume of space. The network transceiver is adapted to forward data received from the tagged medical device to a server if the tagged medical device is inside the volume of space, and to not forward data received from the tagged medical device to the server if the tagged medical device is outside of the volume of space.

According to other aspects of the present disclosure, the network transceiver may be included within the headwall unit and the second location transceiver may be further adapted to receive the data directly from the tagged medical device. Alternatively, the network transceiver may be included within the patient support apparatus and the first location transceiver may be further adapted to receive the data directly from the tagged medical device.

3

In some embodiments, the first and second location transceivers are adapted to use ultra-wideband signals to generate the first and second location estimates, respectively, of the tagged medical device.

In some embodiments, the first and second location transceivers are adapted to use Bluetooth Low Energy (LE) signals to generate the first and second location estimates, respectively, of the tagged medical device.

In some embodiments, the volume of space is defined in a fixed relationship to the headwall unit and does not move when the patient support apparatus moves. In alternative embodiments, the volume of space is defined in a fixed relationship to the patient support apparatus and moves when the patient support apparatus moves.

The controller, in some embodiments, is adapted to change the volume of space based on at least one of the following: a particular room in which the headwall unit is located, a particular type of the patient support apparatus, a particular type of the tagged medical device, or a proximity of a nearby second patient support apparatus.

In some embodiments, the controller is further adapted to determine a distance between the first location transceiver and the second location transceiver in order to determine if the tagged medical device is inside or outside of the volume of space.

In some embodiments, the controller includes a first portion positioned inside the headwall unit and a second portion positioned inside of the patient support apparatus.

The patient support apparatus, in some embodiments, further includes a third location transceiver adapted to generate a third location estimate of the tagged medical device with respect to the patient support apparatus.

A memory, in some embodiments, is included within the system and stores spatial data defining a known position and orientation of the first location transceiver with respect to the third location transceiver. In such embodiments, the controller is further adapted to use the third location estimate and the spatial data when determining if the tagged medical device is inside or outside of the volume of space.

The headwall unit, in some embodiments, includes a third location transceiver adapted to generate a third location estimate of the tagged medical device with respect to the headwall unit.

In some embodiments, the system includes a third location transceiver spaced from the headwall unit wherein the third location transceiver is positioned at a known and fixed location with respect to the headwall unit. In such embodiments, the third location transceiver is adapted to generate a third location estimate of the tagged medical device with respect to the third location transceiver, and the controller is further adapted to use the third location estimate when determining if the tagged medical device is inside or outside of the volume of space.

In some embodiments, the system includes a third location transceiver positioned in a second patient support apparatus. In such embodiments, the third location transceiver is adapted to generate a third location estimate of the tagged medical device with respect to the second patient support apparatus, and the controller is further adapted to use the third location estimate when determining if the tagged medical device is inside or outside of the volume of space.

In some embodiments, the controller is adapted to determine an orientation of the patient support apparatus relative to the headwall unit.

The headwall unit, in some embodiments, includes a first infrared transceiver that is adapted to communicate with a second infrared transceiver onboard the patient support apparatus. In such embodiments, the first and second infrared transceivers are adapted to only be able to communicate with each other when the patient support apparatus is oriented with the second infrared transceiver facing the headwall unit.

The controller, in some embodiments, is adapted to determine at least one of channel state information or angle of arrival information from wireless signals communicated between the tagged medical device and the first location transceiver. In such embodiments, the controller uses the at least one of channel state information or angle of arrival information to generate the first location estimate of the tagged medical device.

In some embodiments, the first location transceiver includes a first antenna array, the second location transceiver includes a second antenna array, and the tagged medical device includes a third antenna array integrated into a tag included within the tagged medical device.

The system, in some embodiments, further includes a second headwall unit. In such embodiments, the second headwall unit includes a third transceiver adapted to wirelessly receive a second set of audio signals from a second patient support apparatus positioned adjacent the second headwall unit; a third location transceiver adapted to generate a third location estimate of the tagged medical device with respect to the second headwall unit; and a second nurse call interface coupled to the nurse call system, wherein the second nurse call interface is adapted to forward the second set of audio signals to the nurse call system.

In some embodiments, the controller is further adapted to communicate with the second headwall unit and to use the third location estimate when determining if the tagged medical device is inside or outside of the volume of space.

In some embodiments, the volume of space is a fixed volume that encompasses one bay of a room but not another bay of the room.

The headwall unit, in some embodiments, is further adapted to receive a volume control message from the patient support apparatus and to respond to the volume control message by sending a command to a television within the room to change its audio volume.

According to another embodiment of the present disclosure, a system is provided for automatically detecting medical devices positioned within a room of a healthcare facility. The system includes a patient support apparatus, a headwall unit, and a controller. The patient support apparatus includes (a) a support surface adapted to support a person; (b) a microphone adapted to convert sound from a patient positioned on the patient support apparatus into audio signals; (c) a first transceiver adapted to wirelessly transmit the audio signals; (d) a first location transceiver adapted to generate a first location estimate of a tagged medical device with respect to the patient support apparatus; and (e) a second location transceiver adapted to generate a second location estimate of the tagged medical device with respect to the patient support apparatus. The headwall unit includes: (i) a second transceiver adapted to wirelessly receive the audio signals from the first transceiver of the patient support apparatus; (ii) a third location transceiver adapted to generate a third location estimate of the tagged medical device with respect to the headwall unit; and (iii) a nurse call interface coupled to a nurse call system, the nurse call interface adapted to forward the audio signals to the nurse call system. The controller is adapted to use the first, second, and third location estimates to determine if the tagged medical device is inside or outside of a volume of space.

In some embodiments, the network transceiver is adapted to forward data received from the tagged medical device to a server if the tagged medical device is inside the volume of space, and to not forward data received from the tagged medical device to the server if the tagged medical device is outside of the volume of space.

In some embodiments, the network transceiver is included within the headwall unit and the second location transceiver is further adapted to receive the data directly from the tagged medical device. In alternative embodiments, the network transceiver is included within the patient support apparatus and the first location transceiver is further adapted to receive the data directly from the tagged medical device.

In some embodiments, the first, second, and third location transceivers are adapted to use ultra-wideband signals to generate the first, second, and third location estimates, respectively, of the tagged medical device.

In some embodiments, the first, second, and third location transceivers are adapted to use Bluetooth Low Energy (LE) signals to generate the first, second, and third location estimates, respectively, of the tagged medical device.

In some embodiments, the volume of space is defined in a fixed relationship to the headwall unit and does not move when the patient support apparatus moves, while in other embodiments, the volume of space is defined in a fixed relationship to the patient support apparatus and moves when the patient support apparatus moves.

The controller, in some embodiments, is adapted to change the volume of space based on at least one of the following: a particular room in which the headwall unit is located, a particular type of the patient support apparatus, a particular type of the tagged medical device, or a proximity of a nearby second patient support apparatus.

In some embodiments, the controller is further adapted to determine a first distance between the first location transceiver and the third location transceiver, to determine a second distance between the second location transceiver and the third location transceiver, and to use the first and second distances to determine if the tagged medical device is inside or outside of the volume of space.

The controller, in some embodiments, includes a first portion positioned inside the headwall unit and a second portion positioned inside of the patient support apparatus.

In some embodiments, the system includes a memory in which is stored spatial data defining a known position and orientation of the first location transceiver with respect to the second location transceiver. In such embodiments, the controller is further adapted to use the spatial data when determining if the tagged medical device is inside or outside of the volume of space.

The headwall unit, in some embodiments, includes a fourth location transceiver adapted to generate a fourth location estimate of the tagged medical device with respect to the headwall unit. In some of these embodiments, the system may further include a memory in which is stored spatial data defining a known position and orientation of the third location transceiver with respect to the fourth location transceiver. The controller, in these embodiments, is further adapted to use the fourth location estimate and the spatial data when determining if the tagged medical device is inside or outside of the volume of space.

In some embodiments, the system includes a fourth location transceiver spaced from the headwall unit and positioned at a known and fixed location with respect to the headwall unit. The fourth location transceiver is adapted to generate a fourth location estimate of the tagged medical device with respect to the fourth location transceiver, and the controller is further adapted to use the fourth location estimate when determining if the tagged medical device is inside or outside of the volume of space.

In some embodiments, the system includes a fourth location transceiver positioned in a second patient support apparatus. In such embodiments, the fourth location transceiver is adapted to generate a fourth location estimate of the tagged medical device with respect to the second patient support apparatus, and the controller is further adapted to use the fourth location estimate when determining if the tagged medical device is inside or outside of the volume of space.

The controller, in some embodiments, is adapted to determine an orientation of the patient support apparatus relative to the headwall unit.

The headwall unit, in some embodiments, includes a first infrared transceiver and the patient support apparatus includes a second infrared transceiver. The first and second infrared transceivers are adapted to only be able to communicate with each other when the patient support apparatus is oriented with the second infrared transceiver facing the headwall unit.

In some embodiments, the controller is adapted to determine at least one of channel state information or angle of arrival information from wireless signals communicated between the tagged medical device and the first location transceiver. In such embodiments, the controller uses the at least one of channel state information or angle of arrival information to generate the first location estimate of the tagged medical device.

In some embodiments, the first location transceiver includes a first antenna array, the second location transceiver includes a second antenna array, the third location transceiver includes a third antenna array, and the tagged medical device includes a fourth antenna array integrated into a tag included within the tagged medical device.

In some embodiments, the system further includes a second headwall unit and the second headwall unit includes: (i) a third transceiver adapted to wirelessly receive a second set of audio signals from a second patient support apparatus positioned adjacent the second headwall unit; (ii) a fourth location transceiver adapted to generate a fourth location estimate of the tagged medical device with respect to the second headwall unit; and (iii) a second nurse call interface coupled to the nurse call system, the second nurse call interface adapted to forward the second set of audio signals to the nurse call system.

The controller, in some embodiments, is further adapted to communicate with the second headwall unit and to use the fourth location estimate when determining if the tagged medical device is inside or outside of the volume of space.

The volume of space, in some embodiments, is a fixed volume that encompasses one bay of a room but not another bay of the room.

The headwall unit, in some embodiments, is further adapted to receive a volume control message from the patient support apparatus and to respond to the volume control message by sending a command to a television within the room to change its audio volume.

According to another aspect of the present disclosure, a patient support apparatus is provided. The patient support apparatus comprises a support surface, a microphone, a first transceiver, a first location transceiver, and a controller. The support surface is adapted to support a person thereon. The microphone is adapted to convert sound from a patient positioned on the patient support apparatus into audio signals. The first transceiver is adapted to pair with a first headwall unit mounted to a headwall of a healthcare facility room, and to wirelessly transmit the audio signals to the first headwall unit when the first transceiver is paired with the first headwall unit. The first headwall unit is adapted to forward the audio signals to a nurse call system. The first location transceiver is adapted to communicate with a second location transceiver incorporated into the first headwall unit in order to generate a first location estimate of the patient support apparatus with respect to the first headwall unit. The first location transceiver is further adapted to communicate with a third location transceiver incorporated into a second headwall unit in order to generate a second location estimate of the patient support apparatus with respect to the second headwall unit. The second headwall unit is spaced from the first headwall unit, and the first location transceiver is adapted to communicate with the third location transceiver while the first transceiver is paired with the first headwall unit. The controller is adapted to use the first and second location estimates to determine a position of a tagged medical device with respect to a volume of space.

According to other aspects of the present disclosure, the volume of space is defined in a fixed relationship to the first and second headwall units and does not move when the patient support apparatus moves. Alternatively, the volume of space may be defined in a fixed relationship to the patient support apparatus and move when the patient support apparatus moves. In some embodiments, the volume of space has a dynamic value and/or boundary, while in other embodiments, the volume of space has static value and/or boundary.

In some embodiments, the first location transceiver is further adapted to communicate with a tag transceiver positioned within a tag of the tagged medical device. In such embodiments, the first location transceiver is adapted to generate a third location estimate of the tagged medical device with respect to the patient support apparatus, and the controller is further adapted to use the third location estimate to determine the position of the tagged medical device with respect to the volume of space.

The patient support apparatus, in some embodiments, further includes a fourth location transceiver adapted to generate a fourth location estimate of the tagged medical device with respect to the patient support apparatus.

In some embodiments, the patient support apparatus includes a network transceiver adapted to forward data received from the tagged medical device to a server if the tagged medical device is inside the volume of space, and to not forward data received from the tagged medical device to the server if the tagged medical device is outside of the volume of space.

The first, second, and third location transceivers, in some embodiments, are adapted to use ultra-wideband signals to generate the first and second location estimates, respectively. Alternatively, or additionally, the first, second, and third location transceivers may be adapted to use Bluetooth Low Energy (LE) signals to generate the first and second location estimates, respectively.

The first headwall unit, in some embodiments, further includes a fourth location transceiver adapted to generate a fourth location estimate of the patient support apparatus with respect to the first headwall unit.

In some embodiments, the first headwall unit includes a first infrared transceiver and the patient support apparatus includes a second infrared transceiver. In such embodiments, the first and second infrared transceivers are adapted to only be able to communicate with each other when the patient support apparatus is oriented with the second infrared transceiver facing the first headwall unit.

The controller, in some embodiments, is adapted to determine at least one of channel state information or angle of arrival information from wireless signals communicated between the first location transceiver and the second location transceiver. The controller uses the at least one of channel state information or angle of arrival information to generate the first location estimate.

In some embodiments, the first location transceiver includes a first antenna array, the second location transceiver includes a second antenna array, and the third location transceiver includes a third antenna array.

In some embodiments, the volume of space encompasses a bay of the healthcare facility room.

The first headwall unit, in some embodiments, is further adapted to receive a volume control message from the patient support apparatus and to respond to the volume control message by sending a command to a television within the healthcare facility room to change its audio volume.

According to another embodiment of the present disclosure, a patient support apparatus is provided that includes a support surface, a first location transceiver, a second location transceiver, and a controller. The support surface is adapted to support a person thereon. The first location transceiver is adapted to generate a first location estimate of a tagged medical device with respect to the patient support apparatus. The second location transceiver is adapted to generate a second location estimate of the tagged medical device with respect to the patient support apparatus. The controller is adapted to use the first and second location estimates, as well as data indicating a spatial relationship between the first and second location transceivers, to determine a position of the tagged medical device with respect to a volume of space.

According to other aspects of the present disclosure, the controller may be in communication with an off-board device adapted to determine a third location estimate of the tagged medical device with respect to the off-board device. In such embodiments, the controller may be adapted to utilize the third location estimate to determine the position of the tagged medical device with respect to the volume of space.

In some embodiments, the controller is further adapted to use a fourth location estimate and a fifth location estimate to determine the position of the tagged medical device with respect to the volume of space. The fourth location estimate is an estimate of a location of the first location transceiver with respect to the off-board device and the fifth location estimate is an estimate of a location of the second location transceiver with respect to the off-board device. The off-board devices may refer to other patient support apparatuses, other headwall units, and/or other devices.

In some embodiments, the first and second location transceivers are both adapted to use a beamforming technique to achieve a directional sensitivity to wireless signals received from the tagged medical device. In some such embodiments, the directional sensitivity is one in which the first and second location transceivers are adapted to receive stronger signals from the tagged medical device when the tagged medical device is in the volume of space as compared to when the tagged medical device is not within the volume of space.

In some embodiments, the patient support apparatus further includes a network transceiver adapted to forward data received from the tagged medical device to a server if the tagged medical device is inside the volume of space, and to not forward data received from the tagged medical device to the server if the tagged medical device is outside of the volume of space. In some such embodiments, the network transceiver may be included within a headwall unit mounted to a headwall of a room of a healthcare facility, and the second location transceiver may further be adapted to receive the data directly from the tagged medical device.

In some embodiments, the network transceiver is included within the patient support apparatus and the first location transceiver is further adapted to receive the data directly from the tagged medical device.

In some embodiments, the first and second location transceivers are adapted to use ultra-wideband signals to generate the first and second location estimates, respectively, of the tagged medical device. Alternatively, or additionally, the first and second location transceivers may be adapted to use Bluetooth Low Energy (LE) signals to generate the first and second location estimates, respectively, of the tagged medical device.

In some embodiments, the patient support apparatus further includes a third location transceiver positioned in a second patient support apparatus, wherein the third location transceiver is adapted to generate a fourth location estimate of the tagged medical device with respect to the second patient support apparatus. In such embodiments, the controller is further adapted to use the fourth location estimate when determining if the tagged medical device is inside or outside of the volume of space.

The controller, in some embodiments, is adapted to determine at least one of channel state information or angle of arrival information from wireless signals communicated between the tagged medical device and the first location transceiver. The controller uses the at least one of channel state information or angle of arrival information to generate the first location estimate of the tagged medical device.

In some embodiments, the first location transceiver includes a first antenna array, the second location transceiver includes a second antenna array, and the tagged medical device includes a third antenna array integrated into a tag included within the tagged medical device.

The patient support apparatus, in some embodiments, includes a microphone and a first transceiver. The microphone is adapted to convert sound from a patient positioned on the patient support apparatus into audio signals. The first transceiver is adapted to wirelessly transmit the audio signals to a headwall unit mounted to a wall of a room of a healthcare facility. The headwall unit includes a second transceiver and a nurse call interface. The second transceiver is adapted to wirelessly receive the audio signals from the patient support apparatus, and the nurse call interface is adapted to forward the audio signals to a nurse call system.

The headwall unit, in some embodiments, is further adapted to receive a volume control message from the patient support apparatus and to respond to the volume control message by sending a command to a television within the room to change its audio volume.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
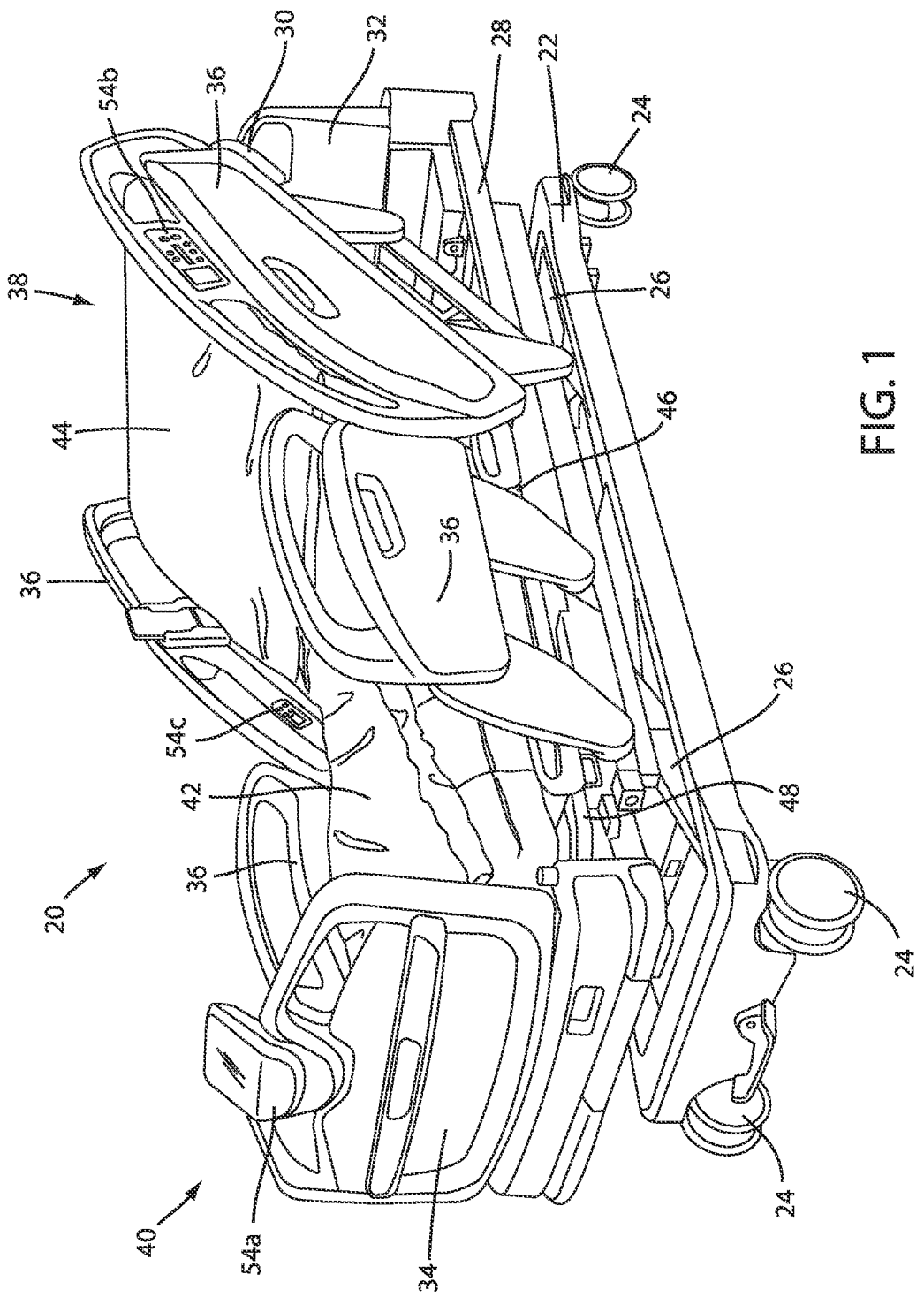
FIG. 1 is a perspective view of a patient support apparatus according to a first embodiment of the present disclosure.

An illustrative patient support apparatus 20 according to an embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant. In some embodiments, the mattress 42 includes one or more inflatable bladders that are controllable via a blower, or other source of pressurized air. In at least one embodiment, the inflation of the bladders of the mattress 42 is controllable via electronics and built into patient support apparatus 20. In one such embodiments, mattress 42 may take on any of the functions and/or structures of any of the mattresses disclosed in commonly assigned U.S. Pat. No. 9,468,307 issued Oct. 18, 2016, to inventors Patrick Lafleche et al., the complete disclosure of which is incorporated herein by reference. Still other types of mattresses may be used.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the construction of patient support apparatus 20 may include the same, or nearly the same, structures as the Model 3002 S3 bed manufactured and sold by Stryker Corporation of Kalamazoo, Michigan. This construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. In still another embodiment, the construction of patient support apparatus 20 may include the same, or nearly the same, structure as the Model 3009 Procuity MedSurg bed manufactured and sold by Stryker Corporation of Kalamazoo, Michigan. This construction is described in greater detail in the Stryker Maintenance Manual for the 3009 Procuity MedSurg bed (publication 3009-009-002, Rev. A.0), published in 2020 by Stryker Corporation of Kalamazoo, Michigan.

It will be understood by those skilled in the art that patient support apparatus 20 can be designed with still other types of constructions, such as, but not limited to, those described in commonly assigned, U.S. Pat. No. 7,690,059 issued Apr. 6, 2010, to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall construction of patient support apparatus 20 may also take on still other forms different from what is disclosed in the aforementioned references provided the patient support apparatus includes the functions and features discussed in greater detail below.

Figure 2:
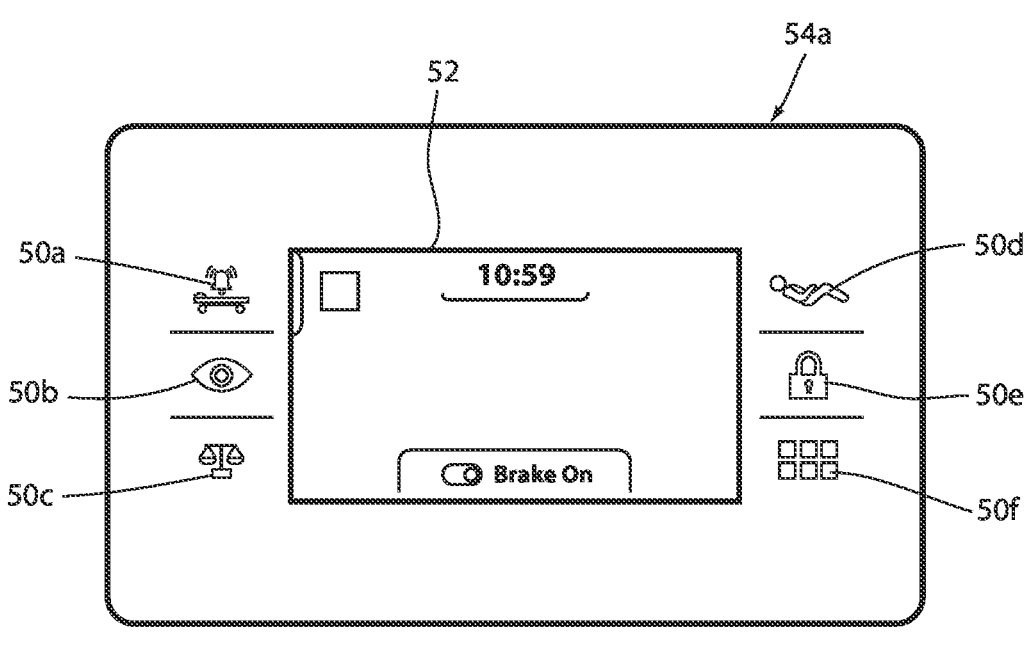
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54*a*, a pair of outer siderail control panels 54*b* (only one of which is visible), and a pair of inner siderail control panels 54*c* (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54*a* allow a user to control one or more of the following: change a height of support deck 30, raise or lower head section 44, activate and deactivate a brake for wheels 24, arm and disarm an exit detection system 56 (FIG. 5) and, as will be explained in greater detail below, communicate with the particular IT infrastructure installed in the healthcare facility in which patient support apparatus 20 is positioned. One or both of the inner siderail control panels 54*c* also include at least one control that enables a patient to call a remotely located nurse (or other caregiver). In addition to the nurse call control, one or both of the inner siderail control panels 54*c* also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54*c* include, but are not limited to, the volume, the channel, the closed-captioning, and/or the power state of the television. With respect to the room and/or night lights, the features that may be controlled by one or more controls 50 on control panel 54*c* include the on/off state and/or the brightness level of these lights.

Figure 5:
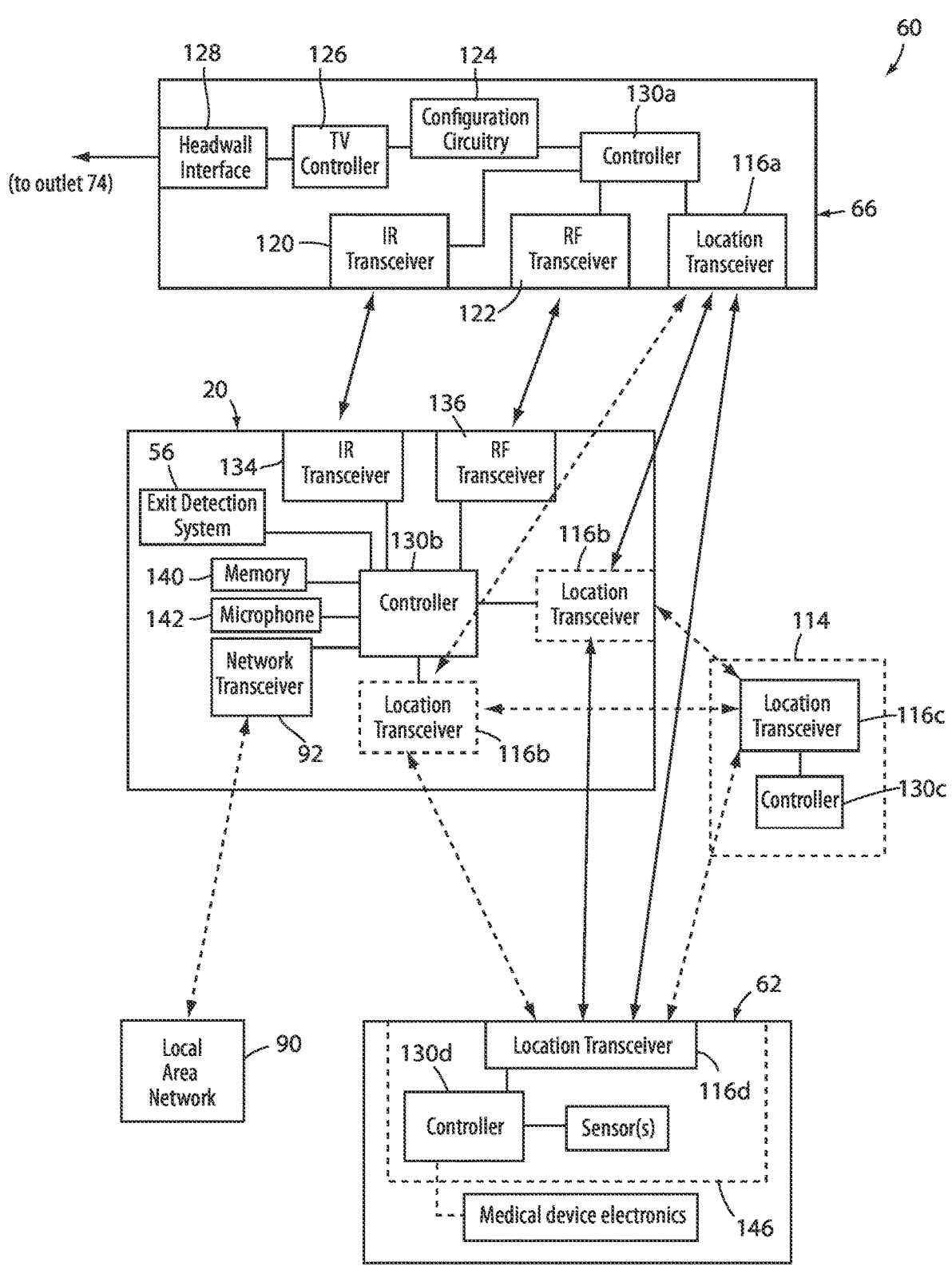
FIG. 5 is a block diagram of several components of the system of FIG. 4.

Control panel 54*a* includes a display 52 (FIG. 2) configured to display a plurality of different screens thereon. Surrounding display 52 are a plurality of navigation controls 50*a-f* that, when activated, cause the display 52 to display different screens on display 52. More specifically, when a user presses navigation control 50*a*, control panel 54*a* displays an exit detection control screen on display 52 that includes one or more icons that, when touched, control an onboard exit detection system 56 (FIG. 5). The exit detection system 56 is as adapted to issue an alert when a patient exit from patient support apparatus 20. Exit detection system 56 may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems may be included within patient support apparatus 20.

When a user pressed navigation control 50*b* (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20.

When a user presses navigation control 50*c*, control panel 54*a* displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system may utilize the same force sensors that are utilized by the exit detection system 56, or it may utilize one or more different sensors. Other scale systems besides those mentioned above in the '254 and '954 applications may alternatively be included within patient support apparatus 20.

When a user presses navigation control 50*d*, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20.

When a user presses navigation control 50*e*, control panel 54*a* displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosure of which is incorporated herein by reference. Other types of motion lockouts may be included within patient support apparatus 20.

When a user presses on navigation control 50*f*, control panel 54*a* displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of menus and/or settings may be included within patient support apparatus 20. In at least one embodiment, utilization of navigation control 50*f* allows a user to navigate to a screen that enables a user to configure the communication settings between patient support apparatus 20 and a headwall unit 66 (see, e.g. FIGS. 4-5). Examples of the type of communication settings that may be configured in this manner are disclosed in, and illustrated in FIGS. 9-15 of, commonly assigned U.S. patent application Ser. No. 63/026,937 filed May 19, 2020, by inventors Alexander Bodurka et al. and entitled PATIENT SUPPORT APPARATUSES WITH HEADWALL COMMUNICATION, the complete disclosure of which is incorporated herein by reference.

For all of the navigation controls 50a-f (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50a-f. It will also be understood that, although navigation controls 50a-f have all been illustrated in the accompanying drawings as dedicated controls that are positioned adjacent display 52, any one or more of these controls 50a-f could alternatively be touchscreen controls that are displayed at one or more locations on display 52. Still further, although controls 50a-f have been shown herein as buttons, it will be understood that any of controls 50a-f could also, or alternatively, be switches, dials, or other types of non-button controls.

Figure 3:
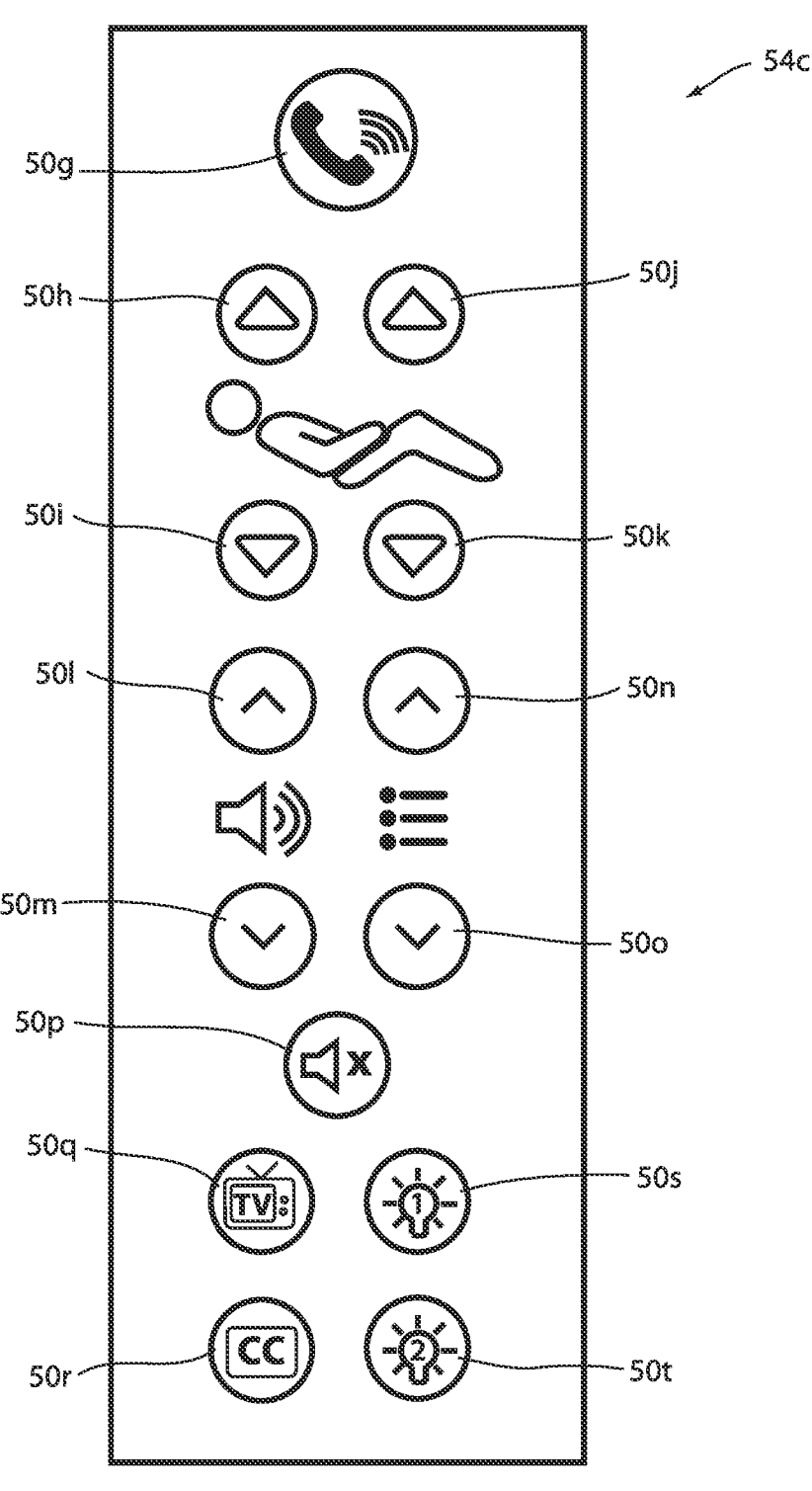
FIG. 3 is a plan view of an illustrative patient control panel of the patient support apparatus of FIG. 1.

FIG. 3 illustrates one example of a patient control panel 54c that may be incorporated into patient support apparatus 20 and positioned at a location on patient support apparatus 20 that is convenient for a patient to access while supported on support deck 30, such as on an interior side of one of the siderails 36. Control panel 54c includes a plurality of controls 50g-t that are intended to be operated by a patient. A nurse call control 50g, when pressed by the patient, sends a signal to a nurse call system requesting that a remotely positioned nurse talk to the patient. A Fowler-up control 50h, when pressed by the patient, causes a motorized actuator onboard patient support apparatus 20 to raise Fowler section 44 upwardly. A Fowler-down control 50i, when pressed by the patient, causes the motorized actuator to lower Fowler section 44 downwardly. A gatch-up control 50j, when pressed by the patient, causes another motorized actuator to raise a knee section of support deck 30, while a gatch-down control 50k causes the motorized actuator to lower the knee section of support deck 30.

A volume-up control 50l, when pressed by the patient, causes patient support apparatus 20 to send a signal to an in-room television instructing it to increase its volume, while a volume down control 50m, when pressed, causes patient support apparatus 20 to send a signal to the television instructing it to decrease its volume. A channel-up control 50n, when pressed by the patient, causes patient support apparatus 20 to send a signal to the television instructing it to increase the channel number, while a channel-down control 50o, when pressed, causes patient support apparatus 20 to send a signal to the television instructing it to decrease the channel number.

A mute control 50p, when pressed, causes patient support apparatus 20 to send a signal to the television instructing it to either mute itself or unmute itself, depending upon whether the television is currently muted or unmuted. In other words, mute control 50p is a toggle control that alternatingly sends mute and unmute commands to the television when it is pressed.

Power control 50q is a toggle control that, when pressed, sends a signal to the television to either turn on or turn off, depending upon the television's current power status. Closed-captioning control 50r is another toggle control that, when pressed, sends a signal to the television to either turn on its closed-captioning feature or to turn off its closed captioning feature, depending upon whether the closed-captioning feature is currently on or off.

Control 50s is a toggle control that, when pressed, sends a signal to a first light to either turn on or turn off, depending upon the current state of that first light. Control 50t is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54c, but also the functions of the controls 50 on control panel 54c, the layout of the controls 50 on control panel 54c, and/or other aspects of control panel 54c may be modified from what is shown in FIG. 3. In some embodiments, control panel 54c is implemented on a pendant controller that includes a cable that is plugged into a port on patient support apparatus 20. In other embodiments, one or more of the controls 50 of control panel 54c may be omitted, augmented, and/or split amongst other controls panels and/or locations. Still other manners of implementing control panel 54c are also possible.

Figure 4:
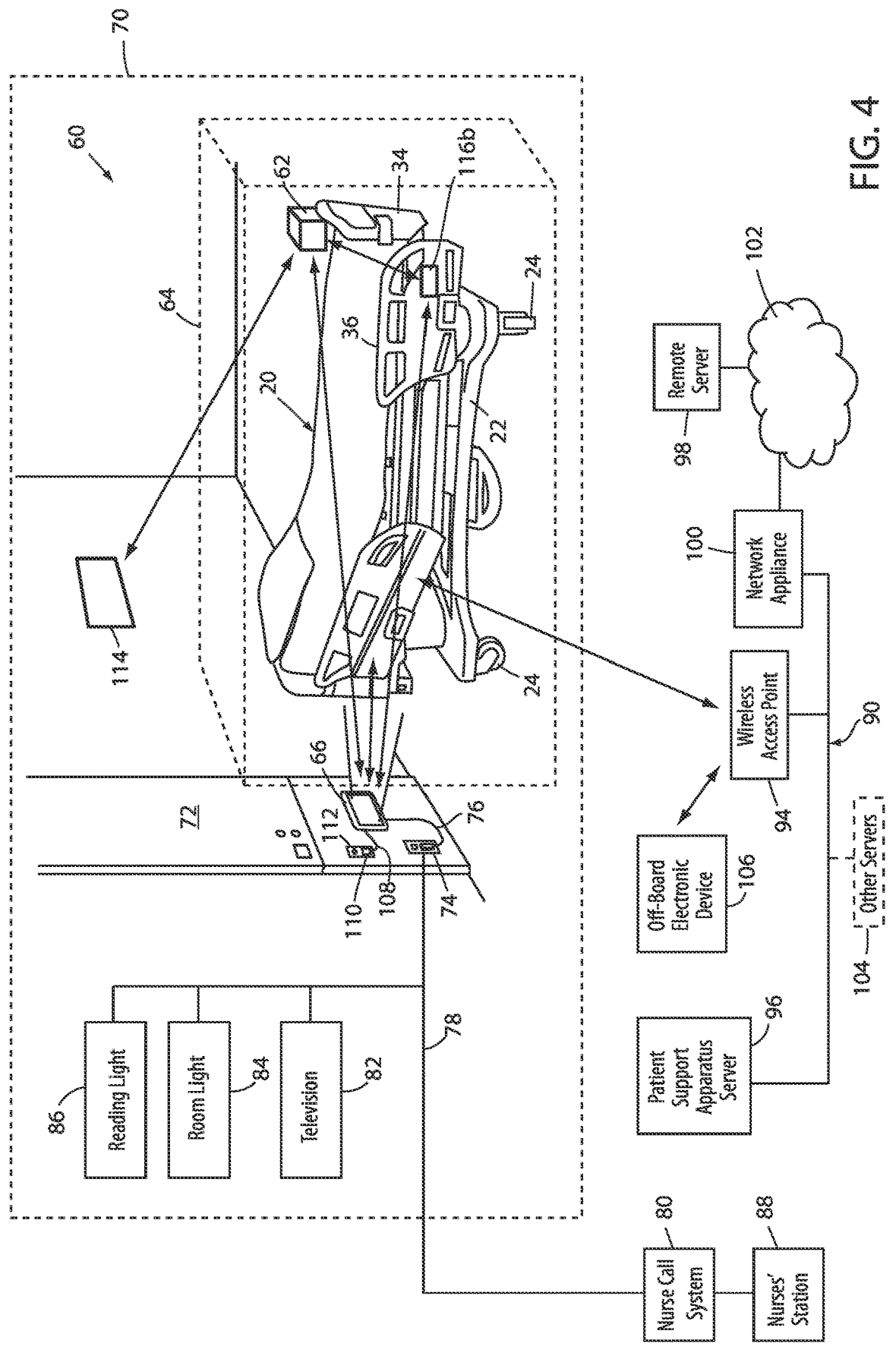
FIG. 4 is a diagram of a first embodiment of a system for automatically detecting the position of tagged medical devices positioned in a room of a healthcare facility.

FIG. 4 illustrates a system 60 for determining the location of one or more tagged medical devices 62 relative to patient support apparatus 20 and/or a volume of space 64 defined within a room 70 of a conventional healthcare facility, such as, but not limited to, a hospital. System 60 includes patient support apparatus 20, one or more headwall units 66, and one or more location transceivers 116. One or more of the location transceivers 116 may be positioned at known and fixed locations within the healthcare facility, and one or more of the location transceivers 116 may also or alternatively be coupled to patient support apparatus 20. When coupled to patient support apparatus 20, location transceivers 116 are positioned therein at known locations on the body of patient support apparatus 20. As will be discussed in greater detail below, location transceivers 116 are adapted to determine if a tagged medical device 62 is positioned within the volume of space 64. If so, system 60 treats the tagged medical device 62 in a first manner, and if not, system 60 treats the tagged medical device 62 in a second and different manner, as will be discussed in greater detail below. In general, if the tagged medical device is positioned inside the space volume 64, system 60 concludes that the device 62 is associated with the patient assigned to that particular patient support apparatus 20 that is also positioned within the same volume of space 64.

As shown in FIG. 4, room 70 includes a headwall 72 into which a conventional communications outlet 74 is physically integrated. Communications outlet 74 is adapted to receive a nurse call cable 76 that physically connects at its other end either to patient support apparatus 20 (not shown) or to a wireless headwall unit 66 (shown in FIG. 4). In many healthcare facilities, communication outlet 74 includes a 37-pin connector, although other types of connectors are often found in certain healthcare facilities. As will be discussed in greater detail below, headwall unit 66 and nurse call cable 76 allow patient support apparatus 20 to communicate with a nurse call system, and one or more room devices positioned within room 70.

Communication outlet 74 is electrically coupled to one or more cables, wires, or other conductors 78 that electrically couple the communication outlet 74 to a nurse call system 80 and one or more room devices, such as a television 82, a room light 84, and/or a reading light 86. Conductors 78 are typically located behind headwall 72 and not visible. In some healthcare facilities, conductors 78 may first couple to a room interface circuit board that includes one or more conductors 78 for electrically coupling the room interface circuit board to room devices 82, 84, 86 and/or nurse call system 80. Still other communicative arrangements for coupling communication outlet 74 to nurse call system 80 and/or one or more room devices 82, 84, 86 are possible.

Room devices 82, 84, 86 are conventional room devices that are typically present in a conventional hospital room. In most cases, the particular brand and model of the television 82 and/or lights 84, 86 will vary from healthcare facility to healthcare facility, and may vary from room to room within the same healthcare facility. The different models and/or brands of televisions 82, room lights 84, and/or reading lights 86 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 82 and/or lights 84, 86 may vary from brand to brand and/or from model to model. Thus, in order for a patient to properly control the television 82 and/or lights 84, 86 using one of the patient control panels 54c, patient support apparatus 20 or headwall unit 66 need to be properly configured to match the particular television 82 and/or lights 84, 86 that are positioned in the same room as the patient support apparatus 20. In the systems described herein, headwall units 66 are configured to match the associated televisions 72 and/or lights 84, 86, as well as the associated nurse call system 80.

Returning to FIG. 4, nurse call cable 76 enables patient support apparatus 20 to communicate with nurse call system 80 and/or room devices 82, 84, 86. A patient supported on patient support apparatus 20 who activates a nurse call control (e.g. 50g; see FIG. 3) on patient support apparatus 20 causes a signal to be wirelessly sent from patient support apparatus 20 to headwall unit 66, which in turn conveys the signal via nurse call cable 76 to the nurse call system 80, which forwards the signal to a one or more remotely located nurses (e.g. nurses at one or more nurses' stations 88). If the patient activates one or more room device controls (e.g. controls 50l-t; see FIG. 3), one or more wireless signals are conveyed to headwall unit 66, which in turn sends appropriate signals via nurse call cable 76 to communication outlet 74 and the room devices 82, 84, 86 that change one or more features of these devices (e.g. the volume, channel, on/off state, etc.).

As is also shown in FIG. 4, patient support apparatus 20 is further configured to communicate with a local area network 90 of the healthcare facility. In the embodiment shown in FIG. 4, patient support apparatus 20 includes a wireless network transceiver 92 (FIG. 5) that communicates wirelessly with local area network 90. Network transceiver 92 is, in at least some embodiments, a WiFi transceiver (e.g. IEEE 802.11) that wirelessly communicates with one or more conventional wireless access points 94 of local area network 90. In other embodiments, network transceiver 92 may be a wireless transceiver that uses conventional 5G technology to communicate with LAN 90, a server hosted thereon, and/or another device. In some embodiments, network transceiver 92 may include any of the structures and/or functionality of the communication modules 56 disclosed in commonly assigned U.S. Pat. No. 10,500,401 issued to Michael Hayes and entitled NETWORK COMMUNICA- TION FOR PATIENT SUPPORT APPARATUSES, the complete disclosure of which is incorporated herein by reference. Still other types of wireless network transceivers may be utilized.

In some embodiments, network transceiver 92 is a wired transceiver that is adapted to allow patient support apparatus 20 to communicate with network 90 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 92 for communicating with network 90 via a wired connection and a wireless transceiver 92 for wirelessly communicating with network 90.

Patient support apparatus 20 is configured to communicate with one or more servers on local area network 90 of the healthcare facility. One such server is a patient support apparatus server 96. Patient support apparatus server 96 is adapted, in at least one embodiment, to receive status information from patient support apparatuses 20 positioned within the healthcare facility and distribute this status information to caregivers, other servers, and/or other software applications. In some embodiments, patient support apparatus server 96 is configured to communicate at least some of the status data received from patient support apparatuses 20 to a remote server 98 that is positioned geographically remotely from the healthcare facility. Such communication may take place via a network appliance 100, such as, but not limited to, a router and/or a gateway, that is coupled to the Internet 102. The remote server 98, in turn, is also coupled to the Internet 102, and patient support apparatus server 96 is provided with the URL and/or other information necessary to communicate with remote server 98 via the Internet connection between network 90 and server 98.

In some alternative embodiments, patient support apparatus 20 may be configured to communicate directly with one or more cloud-based servers, such as remote server 98, without utilizing patient support apparatus server 96. That is, in some embodiments, patient support apparatuses 20 may be configured to communicate directly with a remote server without relying upon any locally hosted servers (e.g. servers hosted on LAN 90). In one such embodiment, patient support apparatus 20 utilizes Microsoft's Azure could computing service to directly connect to one or more remote servers 98 without utilizing server 96. In some such embodiments, network appliance 100 is a router configured to support such direct connections. Still other types of direct-to-cloud connections may be utilized with one or more of patient support apparatuses 20.

As will be discussed in greater detail below, patient support apparatus server 96 may also carry out additional functions, such as, but not limited to, determining the location of one or more tagged medical devices 62 positioned within room 70. Depending upon whether the location of the medical device 62 is within a volume of space 64 defined within the room, and/or within a threshold distance of patient support apparatus 20, patient support apparatus server 96 may be configured to determine whether to allow the medical device 62 to join a wireless network that is associated with the patient assigned to patient support apparatus 20; to automatically associate the tagged medical device 62 (and/or its data) with a particular patient, patient support apparatus, room, and/or bay identifier; to automatically forward data to server 96; and/or to take other actions. In other embodiments, one or more of these functions may be carried out by one or more controllers onboard patient support apparatus 20 or headwall unit 66, and/or a combination of these devices, either alone or in conjunction with server 96 (and/or server 98).

It will be understood that the architecture and content of local area network 90 will vary from healthcare facility to healthcare facility, and that the example shown in FIG. 4 is merely one example of the type of network a healthcare facility may be employ. Typically, additional servers 104 will be hosted on network 90 and one or more of them may be adapted to communicate with patient support apparatus server 96. For example, an electronic health record server will typically be present in any healthcare facility, and in some embodiments discussed herein, it will be in communication with patient support apparatus server 96 in order to receive patient data that is to be recorded in a patient's health record (e.g. weight readings taken from the scales built into patient support apparatuses 20; therapies provided to patients using a powered mattress 42 onboard patient support apparatuses 20, data from a medical device 62 that is determined to be associated with the patient assigned to patient support apparatus 20, etc.). Local area network 90 will also typically allow one or more electronic devices 106 to access the local area network 90 via wireless access points 106. Such electronic devices 106 include, but are not limited to, smart phones, tablet computers, portable laptops, desktop computers, and other types of electronic devices that include a WiFi capability and that are provided with the proper credentials (e.g. SSID, password, etc.) to access network 90 (and, in at least some situations, patient support apparatus server 96).

Headwall units 66 are adapted to wirelessly receive signals from patient support apparatus 20 and deliver the signals to communications outlet 74 in a manner that matches the way the signals would otherwise be delivered to communications outlet 74 if a conventional nurse call cable 76 were connected directly between patient support apparatus 20 and communications outlet 74. In other words, patient support apparatus 20 and headwall unit 66 cooperate to provide signals to communications outlet 74 in a manner that is transparent to communications outlet 74 such that outlet 74 cannot detect whether it is in communication with patient support apparatus 20 via a wired connection or it is in communication with patient support apparatus 20 via a wireless connection between patient support apparatus 20 and headwall unit 66 (the latter of which is in wired communication with outlet 74). In this manner, a healthcare facility can utilize the wireless communication abilities of one or more patient support apparatuses 20 without having to make any changes to their existing communication outlets 74.

In addition to sending signals received from patient support apparatus 20 to communications outlet 74, headwall units 66 are also adapted to forward signals received from communications outlet 74 to patient support apparatus 20. Headwall units 66 are therefore adapted to provide bidirectional communication between patient support apparatus 20 and communications outlet 74. Such communication includes, but is not limited to, communicating command signals from any of controls 50 and/or from any of electronic devices 106 to corresponding room devices 82, 84, and/or 86. Such communication also includes communicating audio signals between a person supported on patient support apparatus 20 and a caregiver positioned remotely from patient support apparatus 20. The audio signals received by headwall units 66 from a microphone on patient support apparatus 20 are forwarded to communications outlet 74, and the audio signals received from communications outlet 74 are forwarded to a speaker onboard patient support apparatus 20.

Nurse call cable 76, in some embodiments, includes a conventional 37 pin connector on each end, one of which is adapted to be inserted into outlet 74 and the other one of which is adapted to be inserted into headwall unit 66. Such 37 pin connections are one of the most common types of connectors found on existing headwalls of medical facilities for making connections to the nurse call system 80 and room devices 82, 84, and 86. Headwall unit 66 and nurse call cable 76 are therefore configured to mate with one of the most common type of communication outlets 74 used in medical facilities. Such 37 pin connectors, however, are not the only type of connectors, and it will be understood that headwall unit 66 can utilize different types of connectors that are adapted to electrically couple to different types of nurse call cables 76 and/or different types of communication outlets 74. One example of such an alternative communications outlet 74 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 74 and corresponding connectors may be utilized.

Headwall unit 66 (FIG. 4) also includes an electrical cord 108 having a plug 110 positioned at a far end that is adapted to be inserted into a conventional electrical outlet 112. Electrical cord 108 enables headwall unit 66 to receive power from the mains electrical supply via outlet 112. It will be appreciated that, in some embodiments, headwall unit 66 is battery operated and cord 108 may be omitted. In still other embodiments, headwall unit 66 may be both battery operated and include cord 108 so that in the event of a power failure, battery power supplies power to headwall unit 66, and/or in the event of a battery failure, electrical power is received through outlet 112.

In addition to any of the structures and functions described herein, headwall units 66 may be configured to communicate location data to patient support apparatus 20 that enables patient support apparatus 20 and/or patient support apparatus server 96 to determine the location of patient support apparatus 20 within the healthcare facility. Such location determination may be carried out in any of the manners disclosed in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall units 66 may also perform additional functions. In some embodiments, headwall units 66 may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. In some embodiments, headwall units 66 may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other embodiments, headwall units 66 may also, or alternatively, perform any of the same functions performed by the headwall units 66 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference.

In some embodiments, headwall units 66 may be constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

In some embodiments, headwall units 66 may also be constructed to include any or all of the functionality of the headwall units disclosed in commonly assigned U.S. patent application Ser. No. 63/026,937 filed May 19, 2020, by inventors Alexander Bodurka et al. and entitled PATIENT SUPPORT APPARATUSES WITH HEADWALL COMMUNICATION, the complete disclosure of which is also incorporated herein by reference.

Still further, in some embodiments, headwall units may be constructed to include any of the features and/or functions of the headwall units 144a disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

In some embodiments, patient support apparatus 20 and/ or patient support apparatus server 96 may include any or all of the functionality of the patient support apparatuses and/or patient support apparatus servers described in any of the aforementioned commonly assigned U.S. patents and/or patent applications.

FIG. 5 depicts in block diagram of various components of one embodiment of system 60. These include patient support apparatus 20, headwall unit 66, a fixed medical device locator 114, and a tagged medical device 62. It will be understood that the components depicted in FIG. 5 are not necessarily a complete set of components, and that system 60 may additionally include one or more additional fixed medical device locators 114, one or more patient support apparatuses, and/or one or more additional headwall units 66. Further, it will be understood that the internal circuitry of each of these components may include more than what is shown in FIG. 5. For example, while headwall unit 66 is depicted in FIG. 5 to include only a single location transceiver 116a, it will be understood that it may include more than one of these. Similarly, although patient support apparatus 20 is depicted as including two location transceivers 116b, it may include more or less than these two. Still other variations of system 60 are possible, including, but not limited to, variations having fewer components than those shown in FIG. 5 (e.g. system 60, in some embodiments, may omit the fixed medical device locator 114) and variations have greater numbers of components.

As was noted, system 60 is adapted to determine if one or more medical devices 62 are positioned within a predefined volume of space 64 (FIG. 4). The predefined volume of space may be defined in a fixed manner relative to the dimensions of the room 70 (and thus stationary), or it may be defined relative to patient support apparatus 20 (and thus moveable as patient support apparatus 20 moves). When defined in fixed manner, volume 64 will typically include the space defined by a particular bay within the room 70. That is, it will encompass the volume typically occupied by the patient support apparatus 20 when the patient support apparatus 20 is in its customary position within a particular bay within the room 70. It will also typically encompass a relatively small amount of space surrounding the customary position of the patient support apparatus 20 (such as, but not limited to, about one to two feet beyond the perimeter of the patient support apparatus 20) in which medical devices 62 might be placed that are used with the patient on patient support apparatus 20 (e.g. an IV stand, patient monitor, etc.). Although FIG. 4 depicts volume 64 as a generally rectangular volume, it will be understood that this is merely one example of the shape that volume 64 may take on. Other non-rectangular shapes and/or shapes having portions that are rectangular and portions that are non-rectangular, as well as still other shape combinations, may be used. Volume 64 generally corresponds to the volume of space in which a medical device 62 must be positioned in order for system 60 to associate it with that particular patient support apparatus 20 (and/or with the patient assigned to that patient support apparatus 20 and/or with the bay or room to which that patient is assigned).

In some embodiments, regardless of whether volume of space 64 is fixed or mobile, the size and/or shape of space volume 64 may be dynamic. That is, the size and/or shape of space 64 may vary in some embodiments. This size and/or shape variance may be based on one or more of the following factors: (a) the particular type, brand, model, or other characteristic of patient support apparatus 20; (b) the particular room, bay, or other environment in which patient support apparatus 20 is currently located; (c) the particular tagged medical device 62 whose location is being determined; and/or (d) the relatively proximity of another patient support apparatus 20. Thus, for example, system 60 is configured in some embodiments to assign larger space volumes 64 to certain models of patient support apparatus 20 that are larger than other models of patient support apparatuses 20. As another example, system 60, in some embodiments, alters the shape and/or enlarges the size of volume 64 in private hospital rooms when compared to the volume 64 that it utilizes in semi-private hospital rooms in which another patient support apparatus 20 is located. Still further, for example, system 60 may utilize larger space volumes 64 for medical devices 62 that are customarily positioned alongside patient support apparatus 20 rather than on patient support apparatus 20 (e.g. mobile IV stands that are supported on the floor versus heel care boots that are worn by the patient). As yet another example, system 60, in some embodiments, may reduce the size of, or otherwise change the shape of, volume 64 when a patient support apparatus 20 is positioned in relatively close proximity to another patient support apparatus 20 in order to avoid mistakenly assigning a tagged medical device 62 to the nearby, but incorrect, patient support apparatus 20. Still other examples of changing the size and/or shape of space volume 64 may be implemented.

Headwall unit 66 (FIG. 5), in some embodiments, includes an infrared transceiver 120, a Bluetooth transceiver 122, a headwall unit controller 130a, configuration circuitry 124, smart television control circuitry 126, and a headwall interface 128. Headwall unit 66 also includes at least one location transceiver 116a that, as will be described more below, is used in conjunction with other location transceivers 116b, 116c, etc. to determine the location of medical device 62. Infrared transceiver 120 is adapted to communicate with an infrared transceiver 134 of patient support apparatus 20 using infrared waves. Bluetooth transceiver 122 is adapted to communicate with Bluetooth transceiver 136 of patient support apparatus 20 using RF waves in accordance with the conventional Bluetooth standard (e.g. IEEE 802.14.1 and/or the standard maintained by the Bluetooth Special Interest Group (SIG) of Kirkland, Washington, USA. In some embodiments, transceivers 122 and 136 utilize Bluetooth Low Energy communications.

Headwall unit controller 130a is adapted to control the operation of transceivers 120, 122, configuration circuitry 124, TV controller 126, headwall interface 128, and location transceiver 116a. Headwall controller 130a and location transceiver 116a together define an "anchor point" that, as will be discussed further below, is adapted to determine the distance (as well as angular information, in some embodiments) between location transceiver 116a and the other location transceivers 116 of system 60. System 60 uses this distance and angular information to repetitively compute the location of tagged medical device 62 and to repetitively determine whether or not it is inside or outside of space volume 64. In some embodiments, location transceiver 116a, as well as the other location transceivers 116, are ultra-wideband transceivers. In other embodiments, location transceiver 116a, as well as the other location transceivers 116, are Bluetooth Low Energy transceivers. In still other embodiments, location transceiver 116a may be combined with RF transceiver 122 such that it is used both to communicate with patient support apparatus 20 and to determine a distance between itself and medical device 62. Location transceiver 116a, as with all of the location transceivers 116 discussed herein, may include an array of antennas that are used to assist in the determination of location. Different manners in which location transceivers 116 may determine the location of tagged medical device 62 are discussed in greater detail in commonly assigned U.S. patent application Ser. No. 63/132,514 filed Dec. 31, 2020, by inventors Alexander Bodurka et al. and entitled PATIENT SUPPORT APPARATUS AND MEDICAL DEVICE NETWORKS, the complete disclosure of which is incorporated herein by reference.

In some embodiments, one or more of the location transceivers 116 and their associated controllers are implemented as any of the Trimension™ ultra-wideband modules available from NXP Semiconductors of Austin, Texas. These modules include, but are not limited to, the Trimension™ UWB modules SR150, SR100T, SR040, NCJ29D5, and/or the OL23DO. Modules manufactured and/or marketed by other companies may also be used, including, but not limited to, the Decawave DWM1000, DWM3000, and/or DWM10001C modules (available from Decawave of Dublin, Ireland); the Nordic TSG5162 SiP module (available from Tsingoal Technology of Beijing, China); and/or the UWB hub, wand, and/or sensors available from Zebra technologies of Lincolnshire, Illinois. Still other types of UWB and/or Bluetooth modules may be used to implement location transceivers 116.

Patient support apparatus 20 includes a controller 130b, a memory 140, the transceivers 134, 136 mentioned above, network transceiver 92, and, in some embodiments, one or more location transceivers 116b. As was noted previously, network transceiver 92 may be a WiFi transceiver, or other type of transceiver, that is adapted to communicate with local area network 90. Each location transceiver 116b of patient support apparatus 20 is positioned at a known location on patient support apparatus 20. This known location information may be stored in memory 140 and/or elsewhere, and may be defined with respect to any suitable common frame of reference. The known location information may include the spatial relationship between transceivers 116b and/or any other components of patient support apparatus 20. For example, in some embodiments, the known location information includes the spatial relationship not only between transceiver 116b themselves, but also the spatial relationships between transceivers 116b and the head end 38 (and/or IR transceiver 134) of patient support apparatus 20. This location information may be used to determine the orientation of patient support apparatus 20 with respect to headwall unit 66, headwall 72, a fixed locator 114, and/or another object or structure within the healthcare facility.

Controller 130b utilizes location transceivers 116b to determine distances between each transceiver 116b and medical device 62, as well as, distances between location transceivers 116b and any off-board location transceivers 116 that are part of system 60 (e.g. location transceivers 116a, 116c). The manners in which these distances may be determined may vary from embodiment to embodiment based upon which type of ultra-wideband or Bluetooth technology is used with location transceivers 116. In general, distances and/or angular information that is generated from the communications between location transceivers 116 may utilize Angle of Arrival (AoA) information, Time of Flight (TOF) information, Channel State Information, and/or other information to generate this information. In some embodiments, each location transceiver 116 includes an array of antennas that are used to generate this distance and/or angular information.

Patient support apparatus 20 also includes, in at least some embodiments, a microphone 142 that is used to detect the voice of the patient when the patient wants to speak to a remotely positioned nurse. The patient's voice is converted to audio signals by microphone 142 and controller 130b is adapted to forward these audio signals to communications outlet 74. When a cable 76 is coupled between patient support apparatus 20 and outlet 74, controller 130b forwards these audio signals to outlet 74 via the cable. When no such cable 76 extends between patient support apparatus 20 and outlet 74, controller 130b wirelessly forwards these audio signals to headwall unit 66 (using transceiver 122 and/or 120) and controller 130a of headwall unit 66 forwards these audio signals to outlet 74. As was noted, outlet 74 is in electrical communication with a conventional nurse call system 80 that is adapted to route the audio signals to the correct nurse's station, and/or other location. In some embodiments, microphone 142 acts as both a microphone and a speaker. In other embodiments, a separate speaker may be included in order to communicate the voice signals received from the remotely positioned nurse. In some embodiments, the audio communication between patient support apparatus 20 and communications outlet 74 is carried out in any of the manners, and/or includes any of the structures, disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

Fixed locator 114 also includes a location transceiver 116c and a controller 130c. Controller 130c, like controller 130b of patient support apparatus 20, controls location transceiver 116c to determine the distance and/or angular orientation between locator transceiver 116c and medical device 62, as well as, in some embodiments, the distance and/or angular orientation between location transceiver 116c and one or more of the other transceivers 116 of system 60.

After the installation of fixed locators 114 in a particular healthcare facility, the location of each fixed locator 114 is recorded. Similarly, after the installation of each headwall unit 66 in the particular healthcare facility, the location of each headwall unit 66 is recorded. The locations of headwall units 66 and fixed locators 114 are recorded in a common frame of reference (or converted to a common frame of reference after recordation). Thus, each headwall unit 66 knows its location within the healthcare facility (e.g. the room number, bay number, height and location on the headwall 72, and position and orientation relative to any nearby fixed locators 114, as well as its position and orientation relative to any nearby other headwall units 66). Similarly, each fixed locator 114 knows its location within the healthcare facility (e.g. room number, bay number, height and location on whatever wall or other structure it is attached to), as well as its position and orientation relative to any nearby other fixed locators 114 and/or headwall units 66. The term "nearby" is used to refer to locators 114 and/or headwall units 66 that are within communication range of each other, in some embodiments.

The location information of a particular fixed locator 114 may be stored in a memory onboard that particular fixed locator 114 and/or it may be stored in a memory onboard other fixed locators 114, onboard headwall units 66, and/or memory 140 of patient support apparats 20. Similarly, the location information of a particular headwall unit 66 may be stored in a memory onboard that particular headwall unit 66 and/or it may be stored in a memory onboard other headwall units 66, onboard fixed locators 114, and/or memory 140 of patient support apparatus 20. If this location information is only stored locally (e.g. onboard the particular device whose location the information corresponds to), this location information is communicated between transceivers 116 as needed in order the transceivers 116 to determine their location relative to each other and the location of tagged medical device 62.

Tagged medical device 62 includes a tag 146 that includes a location transceiver 116d and, in at least some embodiments, a controller 130d. Also, in some instances, tagged medical device 62 includes one or more sensors 148 that gather data regarding the patient with whom the medical device is being used. The particular data gathered by sensors 148 may vary widely depending upon the particular medical device 62. In some instance, sensors 148 may gather vital sign information, device usage information, diagnostic data, pharmaceutical data, movement data, sleep data, and/or still other data regarding the patient and/or the medical device 62 itself. Controller 130d, like controllers 130a, 130b, and 130c, controls location transceiver 116d to determine the distance and/or angular relationship between medical device 62 and the other location transceivers 116a, 116b, and 116c positioned within communication range. This distance and/or angular information is processed by one or more of controllers 130a-d to determine the position of tagged medical device 62, and to further determine whether it is inside or outside of volume 64. The determination of the position of tagged medical device 62 may be carried out by any of controller 130a-d, either in part or in whole. In still other embodiments, information from these transceivers 116a-d may be forwarded to a server, such as patient support apparatus server 96, and the location of medical device 62 may be calculated by server 96.

Each of location transceivers 116a, 116b, 116c, and 116d are, in at least one embodiment, ultra-wideband transceivers that are adapted to determine the aforementioned distances using time of flight, angle of arrival, and/or other characteristics of the signals exchanged between themselves. In another embodiment, each of these transceivers 116a, 116b, 116c, and 116d are Bluetooth Low Energy transceivers that are adapted to determine the distances between themselves using angle of arrival and/or channel state information. Still further, in some embodiments, location transceivers 116a-d may utilize both ultra-wideband and Bluetooth communications to determine their relative locations.

From this relative location information, as well as the knowledge of the position of fixed headwall unit 66 and fixed locators 114, one or more controllers are able to determine the position of medical device 62 relative to the defined space 64. As was noted before, the one or more controllers may include any one or more of controller 130a, 130b, 130c, and/or 130d, and/or it may include a controller integrated into server 96 (or another server). When system 60 includes one or more location transceivers 116b positioned onboard patient support apparatus 20, those location transceivers 116b determine their location and/or orientation with respect to one or more off-board location transceivers 116 (e.g. 116a, 116c, and/or 116b (from other patient support apparatuses 20)), and then use this information to correlate the stationary frame of reference in which the off-board location transceivers 116 are positioned at known locations to the mobile frame of reference that is defined with respect to patient support apparatus 20 (and in which the position of patient support apparatus transceivers 116b are known). Thus, the communication between the off-board transceivers 116 and the on-board transceivers 116 enables the frame of the reference of the patient support apparatus to be determined with respect to the room's (or bay's) frame of reference, and/or vice versa.

Each of controllers 130a, 130b, 130c, and 130d may take on a variety of different forms. In the illustrated embodiment, each of these controllers is implemented as a conventional microcontroller. However, these controllers may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 130a, 130b, 130c, and 130d when carrying out the functions described herein, as well as the data necessary for carrying out these functions, are stored in a corresponding memory that is accessible to that particular controller 130a, 130b, 130c, and 130d. In some embodiments, one or more of the controllers 130a-d are separate from the conventional ultra-wideband modules discussed above that are available from different companies, while in other embodiments, one or more of the controllers 130a-d are integrated into one or more of these conventional ultra-wideband modules.

Figure 6:
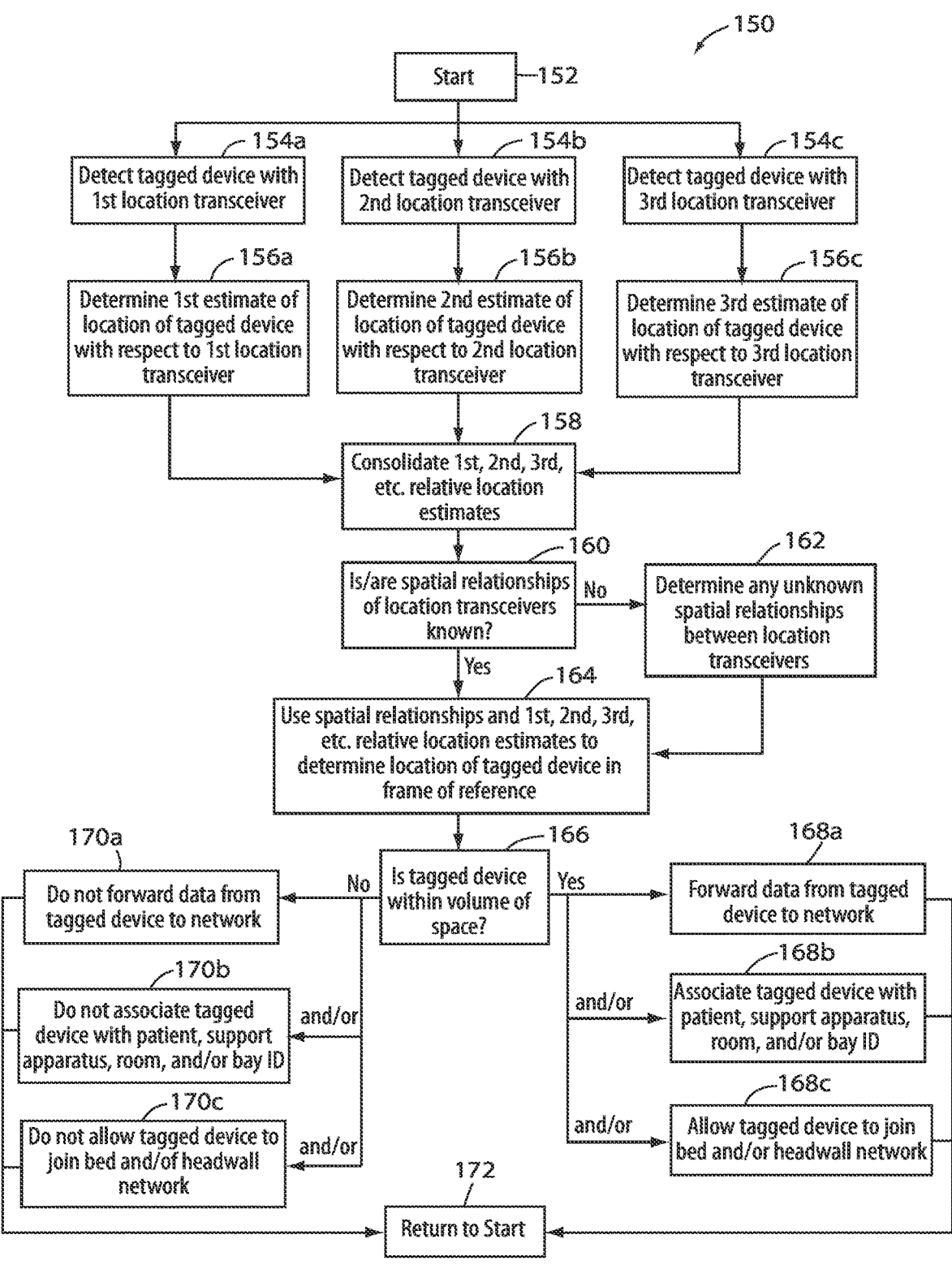
FIG. 6 is a flow diagram of an algorithm implemented by at least one embodiment of the system for automatically detecting the position of tagged medical devices.

FIG. 6 illustrates one example of a control algorithm 150 followed by system 60. Control algorithm 150 may be carried out by any one or more of controllers 130a-d and/or a controller integrated into one or more servers (e.g. server 96). Thus, it will be understood that the "controller" referenced in algorithm 150 may refer to any one or more of these controllers, and that the term "controller 130," as used herein, generically refers to any one or more of these controllers.

Algorithm 150 starts at an initial step 152. Although step 152 is identified as a "start" step, it will be understood that, at least in some embodiments, algorithm 150 is continuously and repetitively operating. By continuously and repetitively operating, algorithm 150 is able to automatically detect the presence of a tagged medical device 62 whenever the tagged medical device 62 is moved into range of the various location transceivers 116. Because of this automatic detection, it is not necessary for an individual to take any specific step to initiate algorithm 150, or to take any step to have system 60 automatically detect the presence of tagged medical device 62.

After step 152 (FIG. 6), controller 130 moves to step 154, which comprises sub-steps 154*a-c*. At each of the sub-steps 154*a-c*, the presence of the tagged medical device 62 is detected by each of the location transceivers 116 that are within range of the tagged medical device 62 and that are part of system 60. System 60 may include different numbers of location transceivers 116, and the number of sub-steps of step 154 of algorithm 150 may therefore vary from the three shown in FIG. 6. In other words, although FIG. 6 shows three sub-steps 154*a-c*, it will be understood that, in some situations and/or in some other embodiments, algorithm 150 may include four sub-steps 154*a-d*, or five sub-steps 154*a-e*, or two sub-steps 154 *a-b*, etc. That is, the number of sub-steps of step 154 varies in accordance with the number of location transceivers 116 that are able to, and adapted to, detect the location of a tagged medical device 62 within a region of the healthcare facility.

In the example shown in FIG. 6, there are three location transceivers 116 that detect the presence of the tagged medical device 62 at step 154 (sub-steps 154*a-c*). The position of these three location transceivers 116 may vary from embodiment to embodiment, as will be discussed in greater detail below. For example, in some embodiments, two of the locations transceivers 116 will be integrated into patient support apparatus 20 (i.e. location transceivers 116*b*), and another one will be integrated into a nearby headwall unit 66 (i.e. location transceiver 116*a*). In other embodiments, there may be only a single location transceiver 116*b* onboard patient support apparatus 20, another location transceiver 116*a* integrated into a headwall unit 66, and another location transceiver 116*c* integrated into a stationary locator 114. Still other combinations are possible.

Sub-steps 154*a-c* are carried out using ultra-wideband signals and/or Bluetooth signals. In some embodiments, each location transceiver 116 is configured to repetitively send out interrogation signals to any tagged medical device 62 that is within range of these transceivers 116. Sub-steps 154*a-c* occur when the tagged medical device 62 moves within range of these transceivers 116 and responds to these interrogation messages.

At sub-steps 156*a-c*, each location transceiver 116 determines a location estimate of the tagged medical device 62 with respect to itself. Thus, as with sub-steps 154*a-c*, the number of sub-steps of step 156 will vary according to the number of location transceivers 116 that are implemented in system 60 (or within a particular room or other area of system 60). It will therefore be understood that algorithm 150 may include more than, or less than, the three sub-steps 156*a-c* of step 156, depending upon the particular embodiment and/or implementation within a particular area of system 60.

At sub-steps 156*a-c*, the transceivers 116*a-c* that are not part of tagged medical device 62 send signals back forth to the location transceivers 116*d* that is part of the tagged medical device 62. The transceivers 116*a-d* and their respective controllers 130 use these signals to determine relative position estimates between the tagged medical device 62 and each one of the other location transceivers 116*a-c*. Thus, for example, at sub-step 156*a*, a first position estimate of tagged medical device 62 with respect to a first location transceiver 116*a* positioned on headwall unit 66 is obtained. Continuing with this example, at sub-step 156*b*, a second position estimate of tagged medical device 62 with respect to a second location transceiver 116*b* positioned onboard patient support apparatus 20 is obtained. Continuing further with this example, at sub-step 156*c*, a third position estimate of tagged medical device with respect to a third location transceiver 116*b* also position onboard patient support apparatus 20 is obtained. In different examples, the position estimates may correspond to relative position estimates made with respect to different locations (e.g. a position estimate of medical device 62 with respect to a location transceiver 116*c* positioned on a stationary locator 114, etc.).

After the relative position estimates of sub-steps 156*a-c* are made, the results of each of these position estimates are shared with at least one common controller amongst the various controllers 130*a-d* (or with a controller onboard one or more servers) at step 158. This sharing may take place by transmitting the position estimates via location transceivers 116. That is, location transceivers 116 are not only able to determine the relative positions between each other, but they are also able to transmit data to and from each other. By sharing the position estimates, the common controller is able to combine the different position estimates to generate a single position estimate that is more precise and more accurate than each of the individual position estimates alone. Before combining those position estimates, however, the common controller moves to step 160 where it determines if the relative position of all of the location transceivers 116 are known or not. If they are known, it moves to step 164. If they are not known, it moves to step 162.

At step 162, the unknown relative positions of each and every one of the location transceivers 116 that were used in sub-steps 154*a-c* (and 156*a-d*) are determined. In general, step 162 will only be carried out between location transceivers 116 that are mobile (e.g. location transceivers 116*b* positioned onboard patient support apparatus 20) and the location transceivers 116 (e.g. 116*a*, 116*c*) that are stationary. This is because the relative positions of the stationary location transceivers 116 are determined during the installation of system 60, are fixed, and are recorded in one or more memories that are accessible to the common controller. For example, the relative position of a location transceiver 116*a* positioned in a headwall unit 66 with respect to a location transceiver 116*c* positioned in a stationary locator 114 that is within range of that headwall unit 66 is determined during system installation and stored in memory. It is therefore unnecessary to determine this relative position at step 164 because it is already known. The position of the location transceiver 116*a* within the headwall unit 66 with respect to a location transceiver 116*b* onboard patient support apparatus 20, as one example, however, will not be known because patient support apparatus 20 is mobile and this relative position can change at any time. Controller 130 therefore determines this relative position at step 162 and forwards the results to the common controller.

At step 162 (FIG. 6), controller 130 therefore determines the relative position of each of the location transceivers 116*b* onboard patient support apparatus 20 with respect to each of the in-range off-board location transceivers 116a, 116c. If there are two or more location transceivers 116b onboard patient support apparatus 20, it is not necessary for the controller 130 to determine the relative position of these transceivers 116b because this information is determined during the manufacture of patient support apparatus 20 and stored in memory 140 (and shared with the common controller, as appropriate). All of the relative position estimates that are made at step 162 are forwarded thereafter to the common controller.

At step 164, the common controller combines all of the information from each of the positions estimates received at step 158 and 162, as well as the known information of the spatial relationships between the off-board location transceivers 116a, 116c (if there are more than one of these), as well as the known information of the spatial relationships between the on-board location transceivers 116b (if there are more than one of these) to generate a single position estimate of the tagged medical device within a suitable frame of reference. This combination of position estimate data and known spatial relationship data may be carried out using mathematical techniques that are known to a person skilled in the art, such as, but not limited to, trilateration and/or triangulation.

For example, in some embodiments, each position estimate of tagged medical device 62 with respect to location transceiver 116a, b, or c may generate a distance estimate between the device 62 and each transceiver 116. A single distance estimate may further translate into a position estimate corresponding to a sphere of possible locations of medical device 62 with respect to a single transceiver 116. By combining multiple of the spheres together from different location transceivers 116, the intersection of these multiple spheres can be determined so as to generate a single and more accurate position estimate of the tagged medical device 62. Different and/or more refined mathematical techniques may also or alternatively be used that utilize angular information derived from the relative positions between each transceiver 116 and the tagged medical device 62.

The result of step 164 (FIG. 6) is an estimate of the current position of medical device 62 within a known frame of reference. As was alluded to earlier, this frame of reference may be a stationary frame of reference (e.g. one that is fixed with respect to the room or other location within the healthcare facility) or it may be a mobile frame of reference (e.g. one that moves with the patient support apparatus 20). In some embodiments, a stationary frame of reference is utilized by system 60 if the space volume 64 is stationary, while in other embodiments, a mobile frame of reference is utilized by system 60 if the space volume 64 moves with patient support apparatus 20. In either case, controller 130 is able to combine the position information at step 164 into a common frame of reference by using the known (or measured) positions between those location transceivers 116 that are positioned off-board patient support apparatus 20 and those location transceivers 116 that are position onboard patient support apparatus 20.

After completing step 164, controller 130 determines if the current position estimate of tagged medical device 62 is inside the volume of space 64 or outside the volume of space 64. This is done by consulting one or more memories (e.g. memory 140 of patient support apparatus 20, or a memory stored in a server of LAN 90, or another memory) that store the criteria for defining space volume 64. If controller 130 determines that tagged medical device 62 is positioned inside space volume 64 at step 166, it performs one or more of steps 168a, *b,* and/or c. If controller 130 determines at step 166 that tagged medical device 62 is positioned outside of space volume 64, it performs one or more steps 170a, 170b, and/or 170c.

At step 168a, controller 130 forwards data received from tagged medical device 62 to local area network 90 (such as patient support apparatus server 96, which may then forward the data elsewhere, such as, but not limited to, an electronic medical record server). This data may be forwarded at step 168a in a variety of different manners. In one embodiment, once a tagged medical device 62 is determined to be within space volume 64, it may send data to patient support apparatus 20 (via location transceivers 116d and 116b, or via a separate set of transceivers) and controller 130b will then forward this data to network 90 via its onboard network transceiver 92 at step 168a. In another embodiment, once a tagged medical device 62 is determined to be within space volume 64, it may send data to headwall unit 66 and headwall unit controller 130a will then forward this data to network 90 via its own onboard network transceiver (not shown) at step 168a. In still other embodiments, stationary locators 114 may include their own network transceivers and the tagged medical device 62 may forward its data to one or more of these locators 114, which then forward the data network 90. In still other embodiments, patient support apparatus 20 and/or headwall unit 66 may initiate communication with the tagged medical device 62 at step 168a using a transceiver of a different type than location transceivers 116, at which point data is forwarded using that different type of transceiver to either patient support apparatus 20 or headwall unit 66, and the recipient of that data then forwards it to network 90. Still other data routes are possible.

In addition to, or as an alternative to, forwarding data at step 168a (FIG. 6), controller 130 may react to the determination of medical device 62 being inside space volume 64 by associating the tagged medical device with the patient assigned to patient support apparatus 20 (or a proxy for that patient), as set forth in step 168b. In other words, at step 168b, controller 130 determines that, because the tagged medical device 62 is within the space volume 64, it is to be associated with that particular patient (or his or her proxy). This association may be carried out by controller 130 at step 168b in a variety of different manners. In one manner, controller 130a of headwall unit 66 and/or controller 130b of patient support apparatus 20 sends a message to patient support apparatus server 96 that includes a unique identifier of the medical device 62 along with a unique identifier of patient support apparatus 20 and/or a unique identifier of headwall unit 66. By sending the unique identifier of the medical device 62 with a unique identifier of the patient support apparatus 20 and/or headwall unit 66, server 96 recognizes that the medical device 62 is to be associated with that particular patient support apparatus 20 and/or headwall unit 66. Further, because server 96 knows the location of patient support apparatus 20 and headwall unit 66, it is able to consult a data table correlating that location to a particular patient. This data table may be stored in another server of network 90, such as, but not limited to, an Admission, Discharge, and Transfer (ADT) server, or still another type of server. Further details of how system 60 may associate a unique patient support apparatus identifier and/or a unique headwall unit identifier with a patient, a room, and/or bay are disclosed in commonly assigned U.S. patent application Ser. No. 16/832,760 filed Mar. 27, 2020, by inventors Thomas Durlach et al. and entitled PATIENT CARE SYSTEM, and/or commonly assigned PCT patent application serial number PCT/US2020/039587 filed Jun. 25, 2020, by inventors Thomas Durlach et al. and entitled CAREGIVER ASSISTANCE SYSTEM, the complete disclosures of both of which are incorporated herein by reference. Still other manners of associated medical device 62 to a particular patient also or alternatively be used at step 168*b*.

At step 168*c*, controller 130 allows tagged medical device 62 to join a network of electronic devices positioned within the vicinity of patient support apparatus 20 and/or headwall unit 66. The network includes patient support apparatus 20, the adjacent headwall unit 66, and/or one or more other medical devices 62 that are positioned within space volume 64. In some embodiments, to join this communication network, the tagged medical device 62 must be granted permission rights, such as an access key, or other authorization information, that allows it to join the network. Once joined, tagged medical device 62 is able to communicate data to and from these devices as part of a separate communication network. In some embodiments, the network that system 60 allows medical device 62 to join at step 168*c* is one or more of the mesh networks disclosed in commonly assigned U.S. patent application Ser. No. 16/569,225 filed Sep. 12, 2019, by inventors Alexander Bodurka et al. and entitled PATIENT SUPPORT APPARATUS COMMUNI-CATION SYSTEMS, the complete disclosure of which is incorporated herein by reference. System 60 may allow medical device 62 access to still other types of networks at step 168*c*.

As was noted before, controller 130 may perform any one or more of steps 168*a*, 168*b*, and/or 168*c* as a result of determining that the medical device 62 is positioned within the space volume 64. It will, of course, be understood that system 60 may take one or more additional actions as well. After completing whichever actions it takes as part of step 168, controller 130 moves to step 172 and re-starts algorithm 150, as will be discussed in greater detail below.

If controller 130 determines at step 166 (FIG. 6) that the tagged medical device 62 is not positioned inside of space volume 64, it proceeds to perform any one or more of steps 170*a*, 170*b*, and/or 170*c*, depending upon the particular embodiment of system 60. Steps 170*a*, 170*b*, and 170*c* are, in essence, the opposite of steps 168*a*, 168*b*, and 168*c*, respectively. Thus, if controller 130 performs steps 170*a*, it does not forward (or stops forwarding if it was previously forwarding) data from tagged medical device 62 to server 96 and/or another server on network 90. Similarly, if controller 130 performs step 170*b*, it does not associate (or stops associating if it was previously associating) tagged medical device 62 with the adjacent patient support apparatus 20 (or the patient assigned to that particular patient support apparatus 20, room, and/or bay). And if controller 130 performs step 170*c*, it does not allow (or stops allowing if it was previously allowing) the tagged medical device 62 to join the wireless network mentioned above with respect to step 168*c*.

After completing whichever ones of steps 170*a-c* that system 60 is configured to perform, it moves to step 172 where it returns to start step 152. System 60 then re-performs the steps of algorithm 150 and continues doing so until it is manually terminated. In some embodiments, the frequency at which system 60 cycles through algorithm 150 may be on the order of once a minute, once a second, or multiple times a second. In some embodiments, this frequency or periodicity remains the same throughout the operation of system 60 (i.e. it is static). In other embodiments, system 60 may vary the periodicity of algorithm 150 based upon one or more factors, such as, but not limited to, the presence or absence of one or more tagged medical devices 62 within space volume 64, the number of devices 62 within space volume 64, whether movement of one or more tagged device 62 is detected, the proximity of one or more of the medical device 62 to the borders of the space volume 64, the proximity of one or more of the medical devices 62 to another patient support apparatus 20, the particular room and/or bay in which the patient support apparatus is located, the time of day, etc.

It will be understood that, although system 60 and algorithm 150 have been primarily described herein as pertaining to determining the location of one or more tagged medical devices 62 to a particular patient support apparatus 20, system 60 may be implemented in multiple rooms and/or multiple locations within a healthcare facility for multiple patient support apparatuses 20. Thus, for example, system 60 may include multiple patient support apparatuses 20, multiple space volumes 64 (for each of the rooms, bays, and/or patient support apparatuses), and multiple sets of headwall units 66 and, in some embodiments, fixed locators 114. System 60 may therefore, at any given time, be monitoring the position of one or more medical devices 62 with respect to a first volume 64 and a first patient support apparatus 20 while also monitoring the positions of one or more other medical devices 62 with respect to other patient support apparatuses 20 and their respective space volumes 64.

It will also be understood that medical devices 62 may take on a variety of different forms. For example, medical devices 62 may include, but are not limited to, exercise devices, heel care boots, IV stands and/or poles, infusion pumps, ventilators, patient monitors (e.g. saturated oxygen ($Sp0_2$) monitors, EKG monitors, vital sign monitors, etc.), patient positioning devices (e.g. wedges, turning devices, pumps), ambient sensors (e.g. air temperature, air flow, light, humidity, pressure, altitude, sound/noise), mattress 42, an incontinence pad or one or more sensors adapted to detect patient incontinence, a Holter device adapted to monitor and record a patient's heart signals, a patient ID tag or bracelet worn by the patient that identifies the patient, a caregiver tag or ID bracelet worn by a caregiver that identifies the caregiver, one or more pieces of furniture that a patient may be expected to use, and/or other types of devices. In general, medical devices 62 may include any devices that are used in a medical setting for treating, diagnosing, monitoring, and/or caring for a patient.

FIGS. 7-15 illustrate a number of different examples of the various manners in which system 60 may be implemented. In each of these examples, the corresponding system 60 is adapted to execute algorithm 150 and operate in the manners previously described. The patient support apparatuses 20, headwall units 66, medical devices 62, and stationary locators 114 include the components shown in these devices in FIG. 5, unless otherwise explicitly stated.

Figures 7, 8:
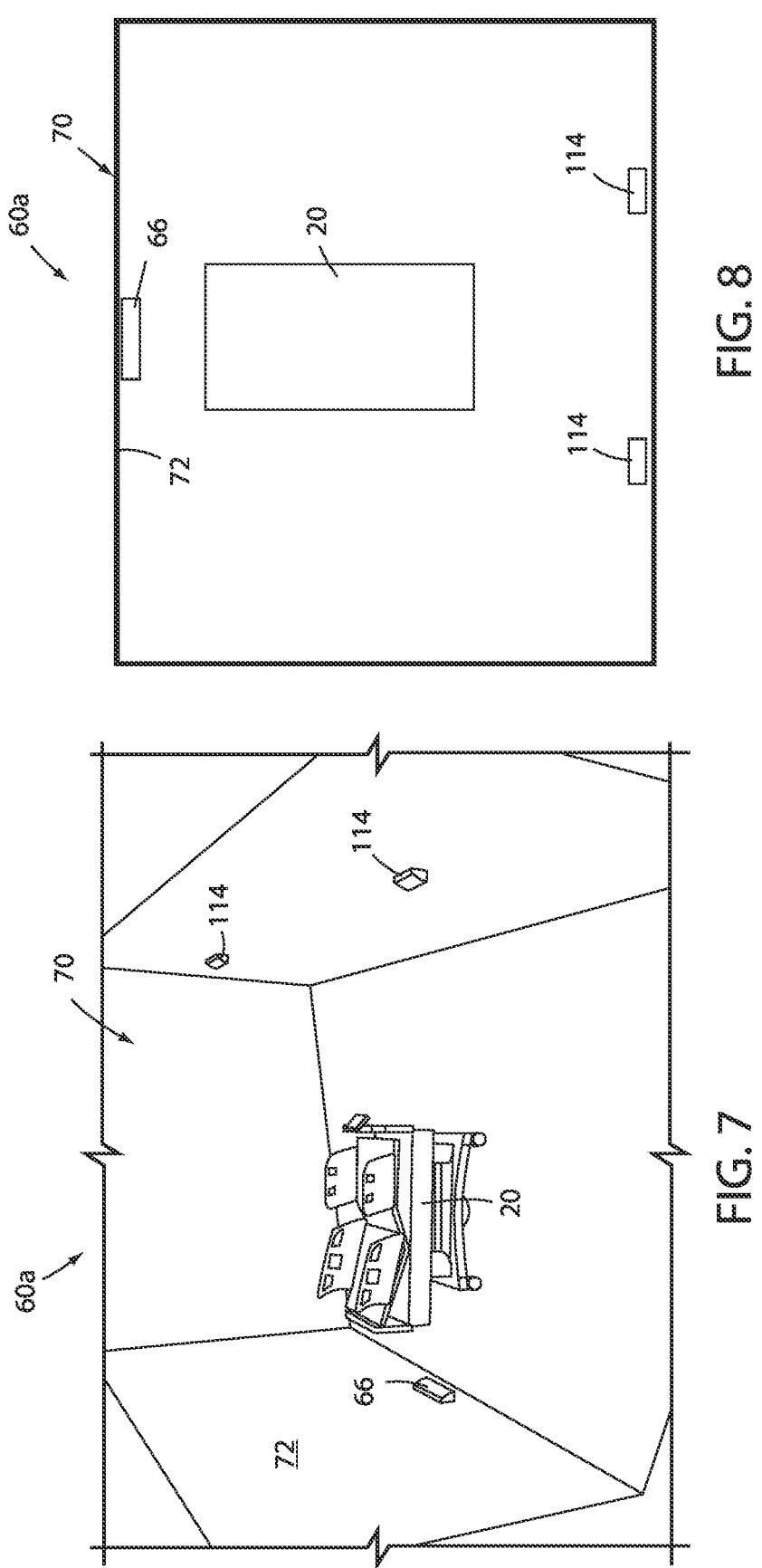
FIG. 7 is a diagram of a second embodiment of the system for automatically detecting the position of tagged medical devices.
FIG. 8 is a block diagram of the patient support apparatus and location transceivers of the embodiment of FIG. 7.

FIGS. 7-8 illustrate a second embodiment of system 60*a* in which the patient support apparatus 20 includes no location transceivers 116. Instead, the location transceivers 116 of this example are positioned inside of the headwall unit 66 and the two fixed locators 114. System 60*a* uses algorithm 150 and the position information gathered from each of the location transceivers 116 in headwall unit 66 and stationary locators 114 to determine the location of a medical device (not shown) with respect to a volume of space 64 (also not shown). Headwall unit 66 of system 60*a*, as with headwall unit 66 of all of the embodiments disclosed herein, functions to not only provide position information regarding one or more tagged medical devices, but it also acts as a communication interface between patient support apparatus 20 and a nurse call system and/or one or more room devices (e.g. television 82, room light 84, and/or reading light 86).

Figures 9, 10:
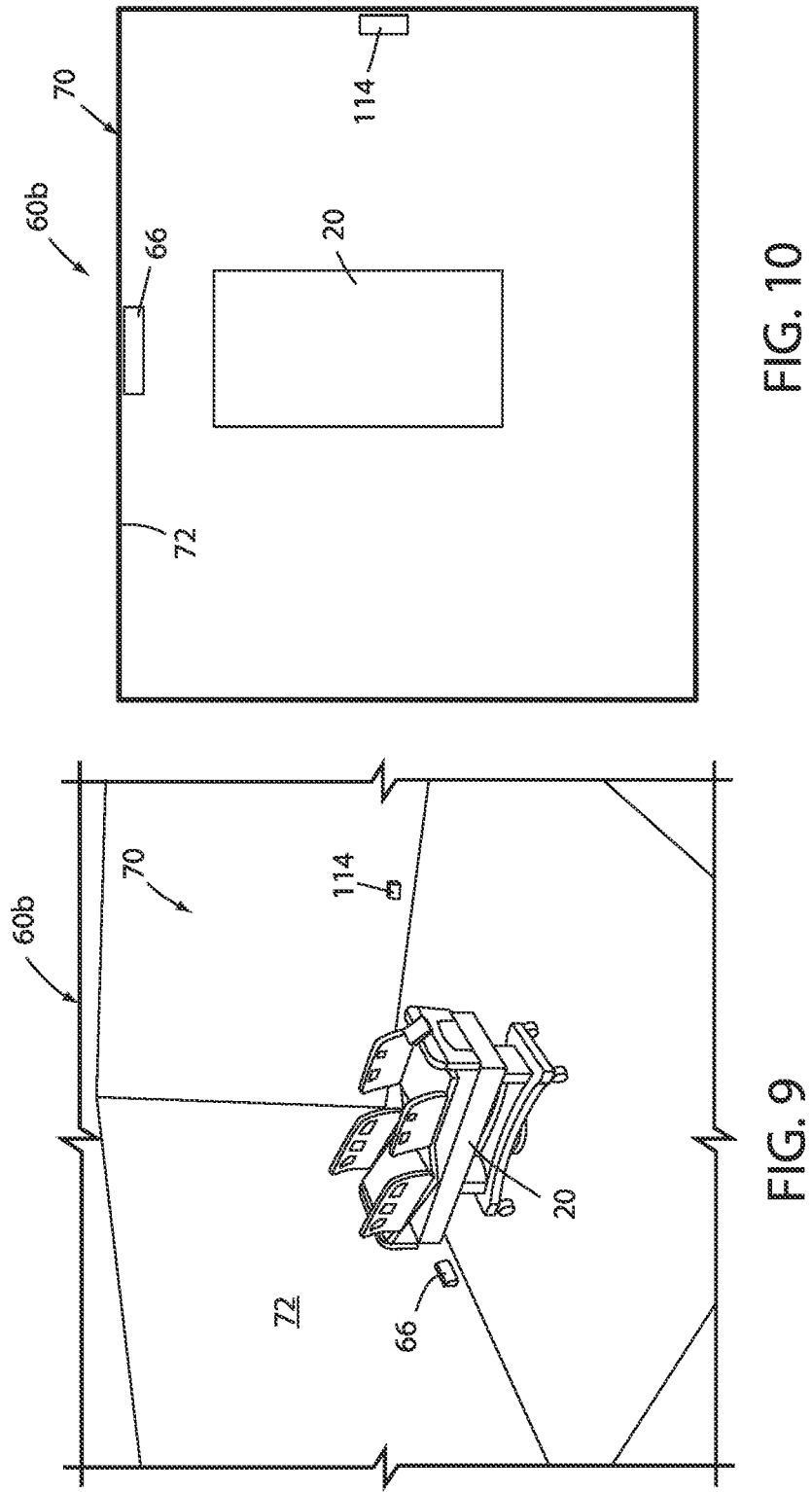
FIG. 9 is a diagram of a third embodiment of the system for automatically detecting the position of tagged medical devices.
FIG. 10 is a block diagram of the patient support apparatus and location transceivers of the embodiment of FIG. 9.

FIGS. 9-10 illustrate a third embodiment of system 60*b* in which the patient support apparatus 20 also includes no location transceivers 116. Instead, the location transceivers 116 of this example are positioned inside of the headwall unit 66 and a single fixed locator 114. System 60*b* uses algorithm 150 and the position information gathered from each of the location transceivers 116 in headwall unit 66 and stationary locator 114 to determine the location of a medical device (not shown) with respect to a volume of space 64 (also not shown). Headwall unit 66 may be modified to include more than one location transceiver 116*a*, in some embodiments.

Figure 12:
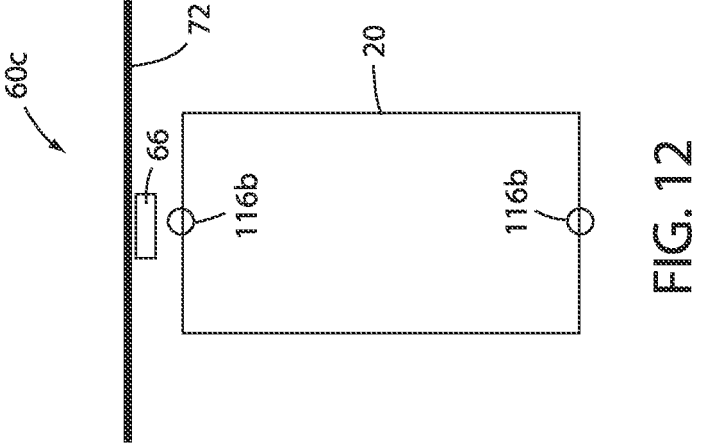
FIG. 12 is a block diagram of the patient support apparatus and location transceivers of the embodiment of FIG. 11.
Figure 11:
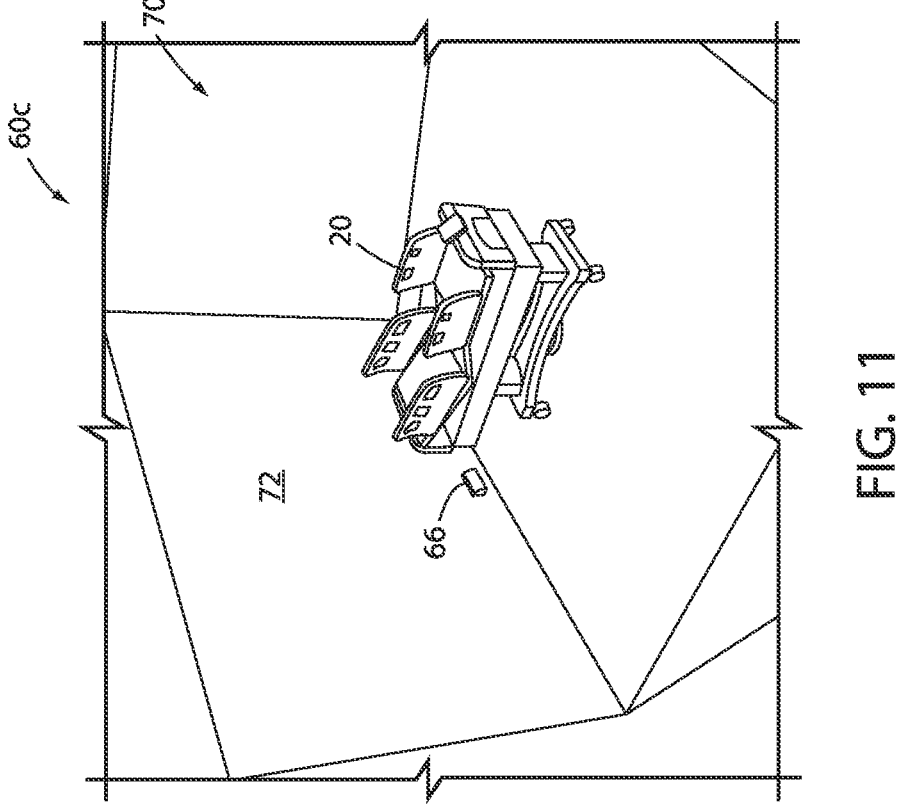
FIG. 11 is a diagram of a fourth embodiment of the system for automatically detecting the position of tagged medical devices.

FIGS. 11-12 illustrate a fourth embodiment of system 60*c*. In this embodiment, patient support apparatus 20 includes two location transceivers 116*b* and headwall unit 66 includes at least one location transceiver 116*a*. System 60*c* uses algorithm 150 and the position information gathered from each of the location transceivers 116 onboard patient support apparatus 20 and in headwall unit 66 to determine the location of a medical device (not shown) with respect to a volume of space 64 (also not shown). Although FIG. 12 depicts a first one of the location transceivers 116*b* positioned at head end 38 and the other one positioned at foot end 40 of patient support apparatus 20, it will be understood that the positions of these location transceivers 116*b* onboard patient support apparatus 20 may be varied from what is shown. Thus, for example, in some embodiments, a first location transceiver 116*b* might be positioned in a first corner of foot end 40 and the other location transceiver 116*b* might be positioned in the opposite corner of foot end 40. Still other variations are, of course, possible. As was described above, regardless of where the position transceivers 116*b* are positioned onboard patient support apparatus 20, memory 140 includes data indicating the spatial relationship of the location transceivers 116*b* relative to each other and a common frame of reference. Still further, in some embodiments, this spatial data indicates the relative position of infrared transceiver 134 (and/or head end 38) relative to the location transceiver(s) 116*b* so that additional position and/or orientation data of patient support apparatus 20 may be gathered from the successful or unsuccessful establishment of a communication link between IR transceivers 134 and 120, as will be discussed further below.

Figures 13, 14:
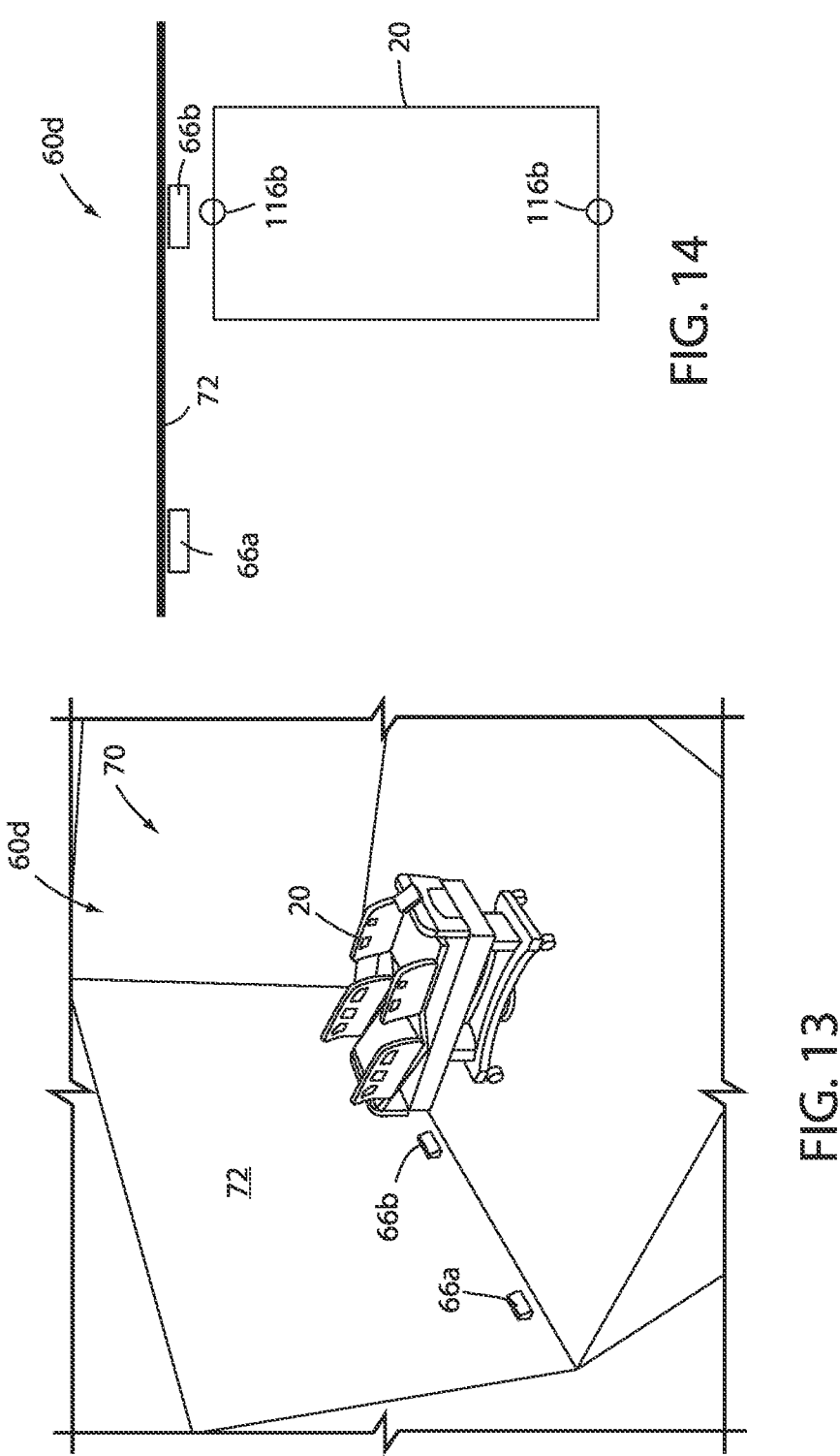
FIG. 13 is a diagram of a fifth embodiment of the system for automatically detecting the position of tagged medical devices.
FIG. 14 is a block diagram of the patient support apparatus and location transceivers of the arrangement of FIG. 13.

FIGS. 13-14 illustrate a fourth embodiment of system 60*d*. In this embodiment, patient support apparatus 20 is shown positioned in a semi-private room that is adapted to accommodate two different patient support apparatuses 20 (although only a single patient support apparatus 20 is shown). That is, room 70 of FIGS. 13-14 is adapted to be occupied by two different patients. It therefore includes two different headwall units 66*a* and 66*b*. One patient support apparatus 20 is intended to be positioned in front of the first headwall unit 66*a* and another patient support apparatus 20 is intended to be positioned in front of the second headwall unit 66*b*. The first patient support apparatus 20 uses the first headwall unit 66*a* to communicate with the nurse call system 80 (and room devices 82-86), but not the second headwall unit 66*b* to communicate with the nurse call system 80 (and room devices 82-86). Similarly, the second patient support apparatus 20 uses the second headwall unit 66*b* to communicate with the nurse call system 80 (and room devices 82-86), but not the first headwall unit 66*a* to communicate with the nurse call system 80 (and room devices 82-86).

Although each patient support apparatus 20 of system 60*d* is adapted to utilize only the headwall unit 66 positioned adjacent its head end 38 for communicating with nurse call system 80 and room devices 82-86, each patient support apparatus 20 is adapted to utilize the location transceivers 116*a* built into both of the headwall units 66 in order to determine the location of a tagged medical device 62. Thus, for example, in the situation illustrated in FIG. 14, patient support apparatus 20 uses only headwall unit 66*b* to communicate with nurse call system 80 and room devices 82-86, but it uses both headwall unit 66*b* and headwall unit 66*a* to determine the location of a tagged medical device 62 (not shown). That is, each location transceiver 116*b* onboard patient support apparatus 20 determines its location relative to not only the location transceiver(s) 116*a* built into headwall unit 66*b*, but also its location relative to each location transceiver 116*a* built into headwall unit 66*a*. These relative position determinations are carried out at step 162 of algorithm 150. During installation of system 60*d*, the position of each headwall unit 66 relative to each other (and relative to room 70) is stored in a memory accessible to controller 130, and this relative position information is used at step 164 to generate the position estimate of a tagged medical device 62.

Patient support apparatus 20 of system 60*d* creates an IR communication link between its IR transceiver 134 and the IR transceiver 120 of headwall unit 66*b*. Similarly, it creates an RF communication link between it RF transceiver 136 and the RF transceiver 122 of headwall unit 66*b*. It does not, however, create any communication links between its IR transceiver 134 or its RF transceiver 136 with any transceivers onboard headwall unit 66*a*. Transceivers 134 and 136 therefore only communicate with the headwall unit that patient support apparatus 20 is positioned in front of (headwall unit 66*b* in FIG. 14). In contrast, location transceivers 116*b* of patient support apparatus 20 communicate with the location transceivers 116*a* onboard both headwall units 66*a* and 66*b*.

Although FIG. 14 illustrates two headwall unit 66*a* and 66*b* that are positioned within the same room, it will be understood that patient support apparatus 20 of system 60*d* may have its location transceivers 116*b* communicate with any headwall units 66 that are within range, regardless of whether or not they are positioned in the same room or not. For example, one or more rooms 70 of system 60*d* may only include a single headwall unit 66, but patient support apparatus 20 may have its location transceivers 116*b* communicate with additional headwall units 66 that are within communication range but not positioned in that same room. In some situations, one or more of the additional headwall units 66 may be positioned on an opposite side of the headwall 72 in a neighboring room wherein the UWB or Bluetooth signals of location transceivers 116*a* and 116*b* are able to penetrate through the headwall 72. Other arrangements may, of course, also be implemented.

Figure 15:
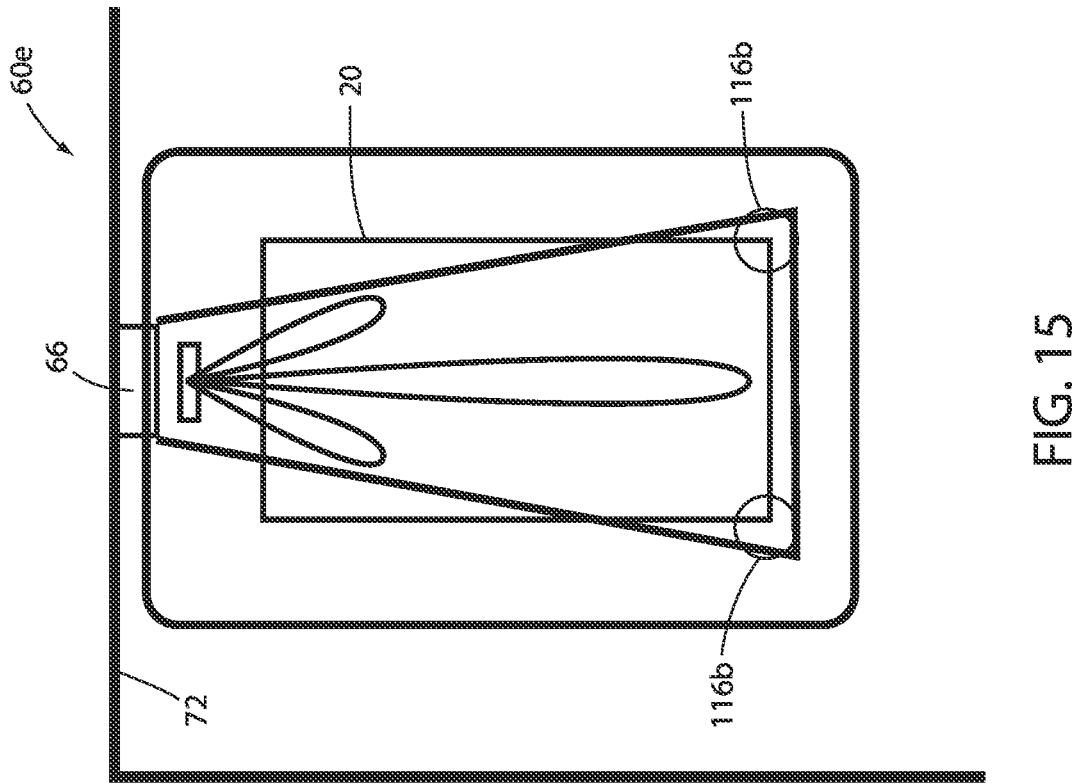
FIG. 15 is block diagram of a patient support apparatus and location transceivers of a sixth embodiment of the system for automatically detecting the position of tagged medical devices.

FIG. 15 illustrates a fifth embodiment of system 60*e*. In this embodiment, patient support apparatus 20 includes one or more directional location transceivers 116*b* that are adapted to communicate with one or more directional location transceivers 116*a* (not shown) positioned inside of headwall unit 66. That is, the location transceivers 116*a* of system 60*e* utilize beamforming and/or other known techniques to limit the areas in which location transceivers 116*a* of headwall unit 66 will be able to successfully communicate with the location transceivers 116*b* of patient support apparatus 20 and/or the location transceiver 116*d* of tag 146. Similarly, the patient support apparatus location transceivers 116*b* may utilize beamforming techniques to limit the areas that they will be able to communicate with headwall unit 66 and/or tagged medical device 62. The limited areas are designed to be areas that include space volume 64. As a result, when the location transceivers 116*a* of headwall unit 66 are able to successfully communicate with the location transceivers 116*b* onboard patient support apparatus 20, then patient support apparatus 20 must be positioned within a relatively small and known area of the room 70. Similarly, when the beamforming location transceivers 116*a* of headwall unit 66 and/or the location transceivers 116*b* of patient support apparatus 20 are able to communicate with the tagged medical device 62, the location of tagged medical device 62 must be within a particular limited space that is defined by the beamforming techniques. The limited spaces in which patient support apparatus 20 and/or medical device 62 may be positioned when these beamforming techniques are used allows controller 130 to make a more accurate determination of the location of a tagged medical device 62 than it otherwise would if beamforming techniques were not utilized.

In some embodiments of system 60*e*, the beamforming techniques used by headwall unit 66 and patient support apparatus 20 may be varied depending upon which particular device these structures are communicating with. For example, when the location transceiver(s) 116*a* of headwall unit 66 communicate with the location transceiver(s) 116*b* of patient support apparatus 20, these location transceivers 116*a, b* may use a first beamforming technique. When either of these sets of transceivers 116*a* or 116*b* communicates with the tagged medical device 62, they may use a second and different beamforming technique. These different beamforming techniques create better spatial sensitivity regarding the potential location of the device 62 with which the location transceiver 116*a* or 116*b* is communicating, as well as better spatial sensitivity regarding the position of patient support apparatus 20 relative to headwall unit 66, both which allow a more refined estimate of the position of device 62 to be determined.

In any of the various embodiments of system 60, controller 130 may be adapted to generate additional information about the position and orientation of patient support apparatus 20 with respect to headwall unit 66 via its communication with the infrared transceiver 120 of headwall unit 66. That is, the infrared transceiver 120 of headwall unit 66 is configured to only be able to successfully communicate with the infrared transceiver 134 of patient support apparatus 20 if head end 38 of patient support apparatus 20 is positioned generally in front of and facing headwall unit 66. This is because IR transceiver 134 of patient support apparatus 20 is attached to the head end of patient support apparatus 20 and because these IR communications rely on an unobstructed line of sight pathway between headwall unit 66 and patient support apparatus 20. Thus, controller 130*b* is able to determine from its successful communication with IR transceiver 120 that its head end is oriented toward headwall 72 (to which headwall unit 66 is mounted), and that it is within the relatively short communication range of headwall unit 66 (e.g. on the order of five to ten feet). This position and orientation information may be combined with the position information obtained from the other location transceivers 116 (e.g. 116*a* of headwall unit 66 and/or 116*c* of stationary locator 114) to determine the location of a tagged medical device 62 relative to a space volume 64.

In at least one embodiment, the aforementioned additional information about the position and orientation of patient support apparatus 20 that is gathered from its communication with infrared transceiver 120 of headwall unit is utilized in conjunction with a system 60 that includes only two location transceivers 116: one positioned onboard patient support apparatus 20 and another positioned onboard headwall unit 66. The location information gathered from these two location transceivers 116*a* and 116*b* is combined with the location information gathered from the infrared communication between patient support apparatus 20, as well as the communication of these two location transceivers 116*a* and 116*b* with the medical device 62, to determine whether medical device 62 is positioned inside or outside of space volume 64.

In any of the various embodiments of system 60, controller 130 may also be adapted to generate additional information about the position of patient support apparatus 20 and/or medical device 62 with respect to one or more other patient support apparatuses 20 that have location transceivers 116*b* that are positioned within communication range. That is, if system 60 determines a location and/or orientation of a first patient support apparatus 20 with respect to a particular room (or other landmark within the healthcare facility), system 60 may have the location transceivers 116*b* aboard the first patient support apparatus 20 communicate with a tagged medical device 62 positioned adjacent a second patient support apparatus 20, and/or communicate with one or more location transceivers 116*b* positioned aboard the second patient support apparatus 20. This communication provides additional estimates of the position of the tagged medical device and/or second patient support apparatus 20, and therefore may be able to provide a more accurate estimate of the position of the tagged medical device vis-a-vis its respective space volume 64.

Figures 16, 17:
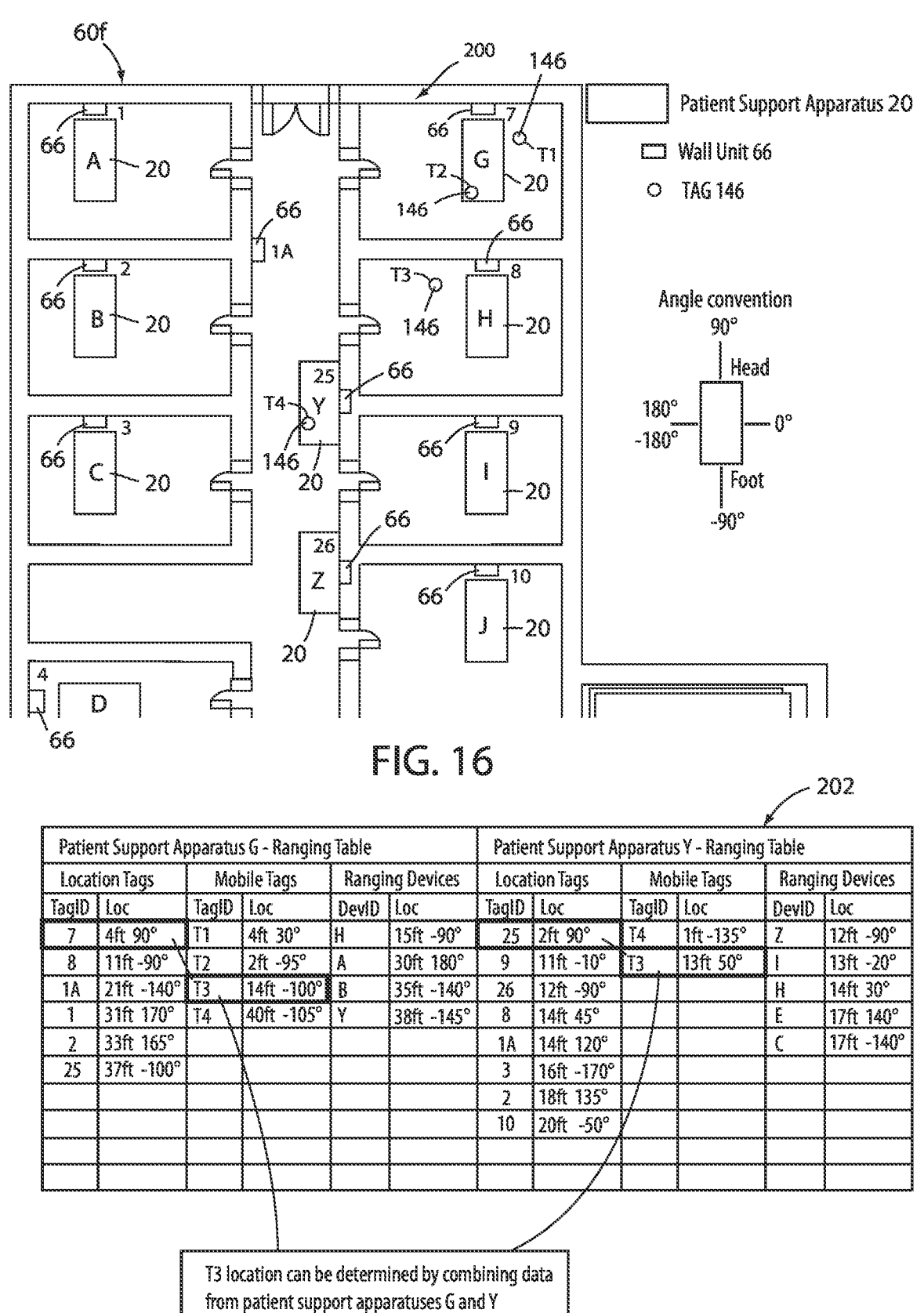
FIG. 16 is a partial healthcare facility floorplan illustrating a seventh embodiment of the system for automatically detecting the position of tagged medical devices.
FIG. 17 is a table of ranging information that the patient support apparatuses of the systems disclosed herein may be configured to generate and send to a central server.

FIG. 16 illustrates a sixth embodiment of system 60*f*. More specifically, FIG. 16 illustrates a section of a healthcare facility floorplan 200 in which are positioned a plurality of patient support apparatuses 20, tags 146, and wall units 66. In this embodiment of system 60*f*, the location of one or more medical device 62 and/or tags 146 are determined by patient support apparatus server 96. That is, each patient support apparatus 20 and/or wall unit 66 is configured to determining ranging information for each of the tags 146 and/or medical devices 62 that are positioned within range of its UWB transceivers. Example of the types of ranging data that may be gathered from each patient support apparatus 20 and/or wall unit 66 is shown in table 202 of FIG. 17. The information shown in table 202 of FIG. 17 is gathered from patient support apparatuses 20 and/or wall unit 66 via their respective UWB communications with tags 146 and/or medical devices 62. Server 96 is configured to use this ranging information to determine the location of each of the UWB devices positioned within the healthcare facility.

As shown in FIG. 17, server 96 may be configured to determine the location of one or more tagged items using ranging information that is received from multiple devices, such as, but not limited to, multiple patient support apparatuses 20. In the particular example of FIG. 17, the ranging information comes from a first patient support apparatus G and a second patient support apparatus Y. Server 96 is configured in at least one embodiment to use the ranging information from these multiple patient support apparatuses 20 to determine the location of another tagged item, such as, but not limited to, a tagged medical device 62.

For example, the location of the tag 146 identified in FIGS. 16 and 17 as tag T3 may be computed from the ranging information from patient support apparatuses G and Y. More specifically, the ranging information includes the position and orientation of patient support apparatus G relative to the wall unit 66 labeled 7 in FIG. 16 (whose location and orientation is known from an initial surveying operation), the position and orientation of tag T3 relative to patient support apparatus G, the position and orientation of patient support apparatus Y relative to the wall unit 66 labeled 25 (whose location and orientation is also known from an initial surveying operation), and the position and orientation of tag T3 relative to patient support apparatus Y. Server 96 uses this position and orientation information to determine the location of tag T3 using conventional geometric and/or trigonometric algorithms.

In other examples, server 96 may be configured to use ranging information from more than two patient support apparatuses 20, and/or ranging information from than two wall unit 66, to determine the location of one or more tags 146. In some embodiments, one or more of the tagged device 62 may be configured to determining ranging information itself and to share that information with patient support apparatus server 96. For example, in one embodiment, a thermal control unit that is adapted to deliver temperature controlled fluid to a patient in order to control the patient's temperature may include control circuitry that performs ranging measurements of the type shown in FIG. 17. Such information is then forwarded to server 96 for use in calculating the location of other tagged objects. The thermal control unit may be of the type disclosed in commonly assigned U.S. patent application Ser. No. 63/122,165 filed Dec. 7, 2020, by inventors Marco Constant et al. and entitled THERMAL CONTROL SYSTEMS WITH DYNAMIC CONTROL ALGORITHMS, the complete disclosure of which is incorporated herein by reference. Still other types of thermal control units may also be used with any of the systems 60 disclosed herein.

It will be understood by those skilled in the art that any of the different configurations of system 60 shown in FIGS. 7-17 may be combined, either wholly or partially, with each other. Some of the combinations may take place throughout an entire healthcare facility, while others of these combinations may take place in only an individual room and/or in other locations. Thus, for example, in some embodiments, some rooms of a particular healthcare facility may include the two headwall units 66 of FIGS. 13-14, as well as, say, a stationary locator 114, such as is shown in system 60b of FIGS. 9-10; while other rooms of the same healthcare facility may include two stationary locators 114 positioned on a first wall in the room (e.g. see FIGS. 7-8) and another stationary locator 114 positioned on a second wall of the room (e.g. see FIGS. 9-10).

As another example, in some embodiments, one or more of the patient support apparatuses 20 may be configured to determine their own relative positions while other patient support apparatuses 20 may be configured to send their ranging information to server 96 in order to allow server 96 to determine their location, such as in the manner discussed above in FIG. 17.

As yet another example, in some embodiments, some patient support apparatuses 20 may include different numbers of location transceivers 116b than other patient support apparatuses 20 located within that same facility. For example, a particular healthcare facility may include some patient support apparatuses 20 having no location transceivers 116b (e.g. FIGS. 7-10) and other patient support apparatuses 20 having one or two location transceivers 116b (e.g. FIGS. 13-14 and FIG. 15). Still further, in some embodiments, any of the patient support apparatuses 20 shown in systems 60a and 60b (FIGS. 7-10) may be modified to include one or more location transceivers 116b. Still other variations and combinations of any of the features and/or functions of the various embodiments of system 60 shown in FIGS. 7-15 may be implemented.

Any of the patient support apparatuses 20 disclosed herein may be modified to include a different number of location transceivers 116b. In at least one embodiment, patient support apparatus 20 includes four location transceivers 116b, each one of which is positioned generally adjacent a different corner of patient support apparatus 20. Other numbers of transceivers 116b may be used. In all of the embodiments, controller 130b has access to data defining the relative position and/or orientation of each of the transceivers 116b on patient support apparatus 20. This position and/or orientation information may be defined in a frame of reference that is common to other landmarks on patient support apparatus 20 and/or that is the same frame of reference used to determine the relative position of a tagged device 62 to patient support apparatus 20.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A system for automatically detecting medical devices positioned within a room of a healthcare facility, the system comprising:

a patient support apparatus comprising:

(a) a support surface adapted to support a person;

(b) a microphone adapted to convert sound from a patient positioned on the patient support apparatus into audio signals;

(c) a first transceiver adapted to wirelessly transmit the audio signals;

(d) a first location transceiver adapted to generate a first location estimate of a tagged medical device with respect to the patient support apparatus;

(e) a third location transceiver adapted to generate a third location estimate of the tagged medical device with respect to the patient support apparatus; and (f) a memory in which is stored spatial data defining a known position and orientation of the first location transceiver with respect to the third location transceiver;

a headwall unit comprising:

(i) a second transceiver adapted to wirelessly receive the audio signals from the first transceiver of the patient support apparatus;

(ii) a second location transceiver adapted to generate a second location estimate of the tagged medical device with respect to the headwall unit; and (iii) a nurse call interface coupled to a nurse call system, the nurse call interface adapted to forward the audio signals to the nurse call system;

a controller adapted to use the first, second, and third location estimates and the spatial data to determine if the tagged medical device is inside or outside of a volume of space; and a network transceiver adapted to forward data received from the tagged medical device to a server if the tagged medical device is inside the volume of space, and to not forward data received from the tagged medical device to the server if the tagged medical device is outside of the volume of space.

2. The system of claim 1 wherein the first and second location transceivers are adapted to use ultra-wideband signals to generate the first and second location estimates, respectively, of the tagged medical device.

3. The system of claim 1 wherein the first and second location transceivers are adapted to use Bluetooth Low Energy (LE) signals to generate the first and second location estimates, respectively, of the tagged medical device.

4. The system of claim 1 wherein the volume of space is defined in a fixed relationship to the patient support apparatus and moves when the patient support apparatus moves.

5. The system of claim 1 wherein the controller is further adapted to determine a distance between the first location transceiver and the second location transceiver in order to determine if the tagged medical device is inside or outside of the volume of space.

6. The system of claim 1 wherein the controller is adapted to determine an orientation of the patient support apparatus relative to the headwall unit.

7. The system of claim 1 wherein the first location transceiver includes a first antenna array, the second location transceiver includes a second antenna array, and the tagged medical device includes a third antenna array integrated into a tag included within the tagged medical device.

8. The system of claim 1 further comprising a second headwall unit, the second headwall unit comprising:

(i) a third transceiver adapted to wirelessly receive a second set of audio signals from a second patient support apparatus positioned adjacent the second headwall unit;

(ii) a third location transceiver adapted to generate a third location estimate of the tagged medical device with respect to the second headwall unit; and (iii) a second nurse call interface coupled to the nurse call system, the second nurse call interface adapted to forward the second set of audio signals to the nurse call system.

\* \* \* \* \*